US010252185B2

(12) United States Patent
Shalliker et al.

(10) Patent No.: US 10,252,185 B2
(45) Date of Patent: Apr. 9, 2019

(54) METHOD AND APPARATUS FOR REACTION CHROMATOGRAPHY

(71) Applicants: THERMO ELECTRON MANUFACTURING LIMITED, Altrincham (GB); UNIVERSITY OF WESTERN SYDNEY, Penrith (AU)

(72) Inventors: Ross Andrew Shalliker, Hornsby (AU); Michelle Camenzuli, Amsterdam (NL); Harald Ritchie, Runcorn (GB)

(73) Assignees: Thermo Electron Manufacturing Limited, Altrincham (GB); University of Western Sydney, Penrith (AU)

( * ) Notice: Subject to any disclaimer, the term of this patent is extended or adjusted under 35 U.S.C. 154(b) by 131 days.

(21) Appl. No.: 13/897,187

(22) Filed: May 17, 2013

(65) Prior Publication Data
US 2013/0306558 A1 Nov. 21, 2013

(30) Foreign Application Priority Data
May 21, 2012 (GB) .................................. 1208901.7

(51) Int. Cl.
*B01D 15/38* (2006.01)
*G01N 30/60* (2006.01)
*G01N 30/84* (2006.01)

(52) U.S. Cl.
CPC ..... *B01D 15/3857* (2013.01); *G01N 30/6017* (2013.01); *G01N 30/84* (2013.01); *G01N 2030/8429* (2013.01)

(58) Field of Classification Search
None
See application file for complete search history.

(56) References Cited

U.S. PATENT DOCUMENTS

2006/0273012 A1   12/2006   Dehmer
2007/0138076 A1*   6/2007   Daridon et al. ........... 210/198.2

FOREIGN PATENT DOCUMENTS

EP   0 257 582 A2   3/1988
EP   0 469 519 A2   2/1992
(Continued)

OTHER PUBLICATIONS

Camenzuli et al., "Active flow management in preparative chromatographic separations: A preliminary investigation into enhanced separation using a curtain flow inlet fitting and segmented flow outlet fitting,9" Journal of Separation Science, vol. 35, No. 3, Feb. 9, 2012, pp. 410-415.
(Continued)

*Primary Examiner* — Kara M Peo
(74) *Attorney, Agent, or Firm* — Nicholas Cairns

(57) ABSTRACT

An apparatus for reaction chromatography comprising: a chromatography column, the column having a fluid outlet for an eluate flow, wherein the fluid outlet is configured with two or more fluid ports, the two or more fluid ports comprising one or more reactant ports, wherein each reactant port is for connecting a reactant flow into the eluate flow to react with the eluate flow, and one or more product ports for receiving the reacted eluate flow; one or more reactant sources in fluid communication with the one or more reactant ports to provide the reactant flow; and one or more processing units in fluid communication with the one or more product ports to process the reacted eluate flow.

12 Claims, 31 Drawing Sheets

(56) References Cited

FOREIGN PATENT DOCUMENTS

| EP | 1653231 A1 | 5/2006 |
|---|---|---|
| JP | 60058543 A | 4/1985 |
| JP | 62063857 A | 3/1987 |
| JP | 62240857 A | 10/1987 |

OTHER PUBLICATIONS

McDermott, G.P., et al., "Screening for antioxidants in complex matrices using high performance liquid chromatography with acidic potassium permanganate chemiluminescence detection," Analytica Chimica Acta, Elsevier, Amsterdam, NL, vol. 684, No. 1-2, Jan. 17, 2011, pp. 134-141.

* cited by examiner

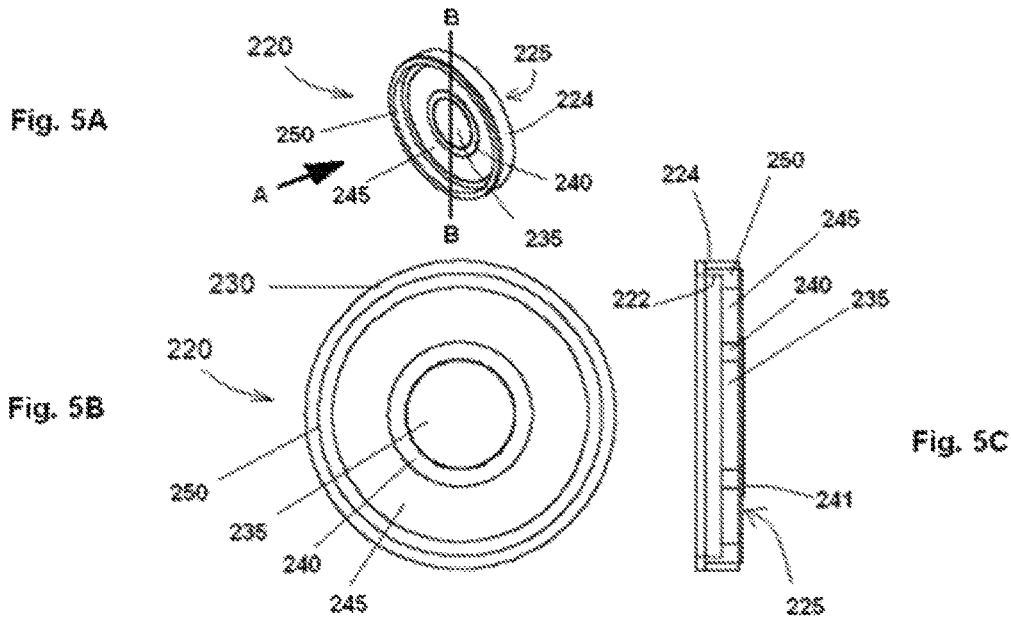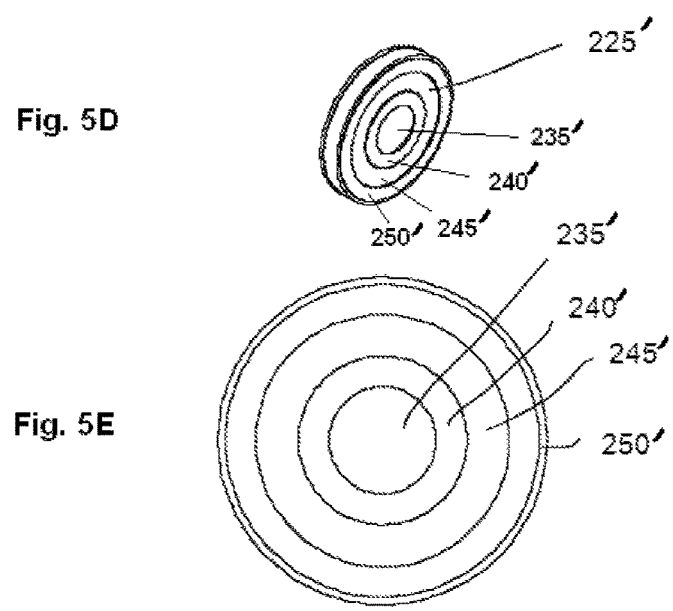

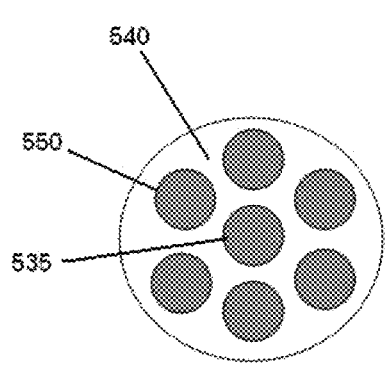
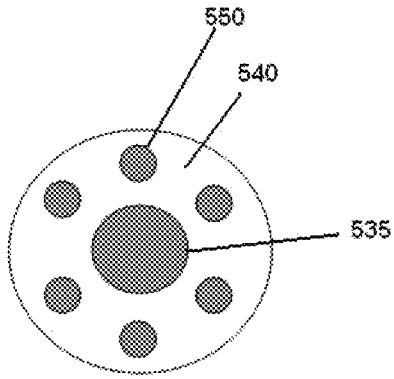
Fig. 5F    Fig. 5G
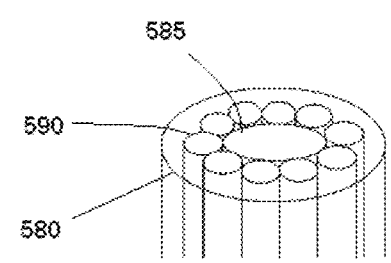
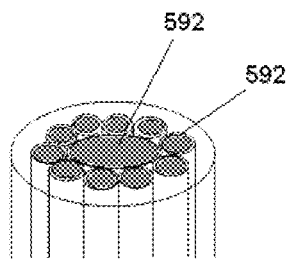
Fig. 5H    Fig. 5I

METHOD AND APPARATUS FOR REACTION CHROMATOGRAPHY

FIELD OF THE INVENTION

This invention relates to the field of chromatography and in particular reaction chromatography.

BACKGROUND OF THE INVENTION

Chromatography columns have been extensively developed and are used routinely in both analytical and preparative chromatography. As is well known, the separation in a chromatography column of a sample (also termed an analyte or solute) comprising a mixture of components is achieved by dissolving the sample in an eluant to form a fluid mobile phase and passing the mobile phase through a stationary phase typically packed within a tubular column, thereby causing the sample to separate into its components due to the differences in the partitioning between the mobile and stationary phases of the different components (i.e. the components have different partition coefficients). The present invention relates to such columns.

The eluant fluid is most commonly a liquid but may be another fluid such as a supercritical fluid (SCF). The present invention relates to columns used with liquid or SCF mobile phases. The term fluid herein thus refers to liquid or SCF. The present invention, for the avoidance of doubt, does not relate to gas chromatography.

In column chromatography the stationary phase is typically in the form of a bed of packed particles or a porous monolithic block within a column. The present invention is applicable to packed columns but it is not limited to only packed columns. Often the columns comprise reusable columns with disposable cartridges, both of which are usually cylindrical (typically circular cross section). The present invention may be used with cylindrical columns (most preferably circular cylindrical columns) or non-cylindrical columns. That is, the wall of the column may have numerous cross-sectional profiles but most preferably has a circular profile in its transverse cross section.

The mobile phase is passed through the column and the mobile phase leaving the column (termed eluate) is detected as a function of time and/or collected as fractions. The detected signal variation with time, i.e. the chromatogram, indicates the presence of different components within the mixture. The degree of separation of the different components depends upon the separation efficiency or resolution of the column. The resolution of the column depends upon many factors. Such factors include the nature of the mobile and stationary phases, which have been extensively studied and developed.

In the technique of reaction chromatography the chemical identities of the sample components are changed by a chemical reaction occurring between sample introduction and sample detection. The reaction can take place upstream of the column such that the chemical identities of the individual components passing through the column differ from those of the original sample, or downstream of the column, i.e. between the column and the detector, such that the original (i.e. unreacted) sample components are separated in the column but their identities are changed prior to being detected by the detector. The reaction can also take place between two columns. For example, a first column may separate enantiomers, and a chemical reaction is targeted to, perhaps just one, or both, enantiomeric species. The reaction occurs, and the second column then separates subsequent products from the reaction.

Applications of reaction chromatography can be found, for example, in the biosciences, particularly in the area of proteomics, as well as in the pharmaceutical and environmental industries. In such applications, analysts will typically perform some type of post-column modification of the samples. For example, post-column derivatisation of the samples is performed to allow detection and analysis of the sample by means of a suitable detector employing, for example fluorescence detection, chemiluminescence detection or a decolorisation reaction, but not limited to these types of detections. The detection method based on the reaction may be more sensitive, compared to detection of the unreacted sample but more importantly the detection methods provide greater detection specificity, i.e. the reaction and associated detection method are specific to certain components of the sample and not others.

In proteomics, often one or two proteins are desired from an entire proteome for further characterization. Analysis of the target proteins has been achieved via two principle processes: top-down or bottom-up proteomics. The former process involves the characterization of intact proteins, whilst the latter involves the use of digestive enzymes followed by the characterization of fragments. Both approaches have used High Performance Liquid Chromatography (HPLC) and a protein modification has been performed as a separate step either before or after the chromatography column.

As each step of a process typically requires more time, labour and cost, the elimination or simplification of any step is economically desirable and may bring about enhancements in sample throughput and processing.

SUMMARY OF THE INVENTION

Against the above background, according to an aspect of the present invention there is provided an apparatus for reaction chromatography comprising: a chromatography column, the column having a fluid outlet for an eluate flow, wherein the fluid outlet is configured with two or more fluid ports, the two or more fluid ports comprising one or more reactant ports, wherein each reactant port is for connecting a reactant flow into the eluate flow to react with the eluate flow, and one or more product ports for receiving the reacted eluate flow; one or more reactant sources in fluid communication with the one or more reactant ports to provide the reactant flow; and one or more processing units in fluid communication with the one or more product ports to process the reacted eluate flow. A processing unit may comprise, for example, a detector, a fraction collector or another chromatography column.

According to another aspect of the present invention there is provided a method of reaction chromatography comprising: providing a mobile phase containing a sample to be separated into components; flowing the mobile phase longitudinally through a chromatography column from an inlet of the column to an outlet of the column to separate the sample into components, the mobile phase leaving the column through the outlet as an eluate flow; introducing a reactant flow into the outlet to react with the eluate flow and receiving the reacted eluate flow from the outlet and processing the reacted eluate flow. The processing may comprise detecting the eluate, collecting fractions of the eluate, or allowing the eluate to flow through the or another chromatography column.

DETAILED DESCRIPTION OF THE INVENTION

In certain preferred embodiments, the method comprises splitting the flow of eluate as it leaves the column through the outlet into at least two separate portions; and processing the at least two separate portions separately. In certain preferred embodiments, the flow of eluate is split as it leaves the column through the outlet into at least two separate portions, each portion leaving via its own fluid port(s), wherein the apparatus is configured to separately process the separate portions. The configuration of the column outlet in this way enables separation of the eluate flow to be performed on-column, not post-column. The separate portions of eluate may have the same composition. In other cases the portions of eluate may have different compositions. One eluate portion may be reacted eluate. Another eluate portion may be unreacted eluate, which passes on unreacted for processing, or may be differently reacted eluate, e.g. eluate reacted with different reactant to the first eluate portion. Each additional eluate portion to the first portion in general may be independently either reacted or not reacted.

In some embodiments, the outlet flow need not necessarily be split into two portions. For example, an embodiment of the invention may be that reactant flow enters a peripheral port in a peripheral region of the outlet, flows through the split where one is present as described hereafter, and exits another port of the outlet, together with outflowing mobile phase. That is, the peripheral reactant 'in' flow combines with the 'out' mobile phase flow, resulting in just the one outlet flow stream.

The reacted eluate and, where present, other portion(s) of eluate advantageously can be processed separately and independently of each other, e.g. detected independently and/or collected in fractions independently. Separate detectors, optimised detectors for each portion of eluate, may therefore be employed.

The eluate is reacted at the outlet of the column so that a separate downstream reactor and reaction step is not required as it is in conventional reaction chromatography. A reaction coil may or may not be used downstream of the column outlet. In addition to the enhanced sample throughput thereby achieved, other advantages of the present invention have been found to include enhanced specificity and yield of reactions in the eluate. A lower noise level in the chromatogram has also been found when using the present invention.

At the outlet, the reactions can be timed to occur when they are required, e.g. to correspond to the appearance at the outlet of a target component. It is advantageous to use an embodiment of the invention to selectively react with only target compounds. Since chromatographic migration of components through the column is predictable, the application of a reactant into the outlet at a particular time can be carried out. In some embodiments, therefore, the invention comprises selecting an eluting component as a target component and introducing the reactant into the column outlet during a time window in which that target component is present at the outlet as it elutes, thereby to react with that target component. This procedure is performed for as many target components as required.

Different reactants may be introduced for different target components at different times. For example, a first reactant may be introduced in the manner described at a time when a first target component elutes at the outlet, a second reactant may be introduced at a time when a second target component elutes at the outlet and so on for as many target components as required, where the second and subsequent reactants may be the same or different from the first reactant. Preferably, the reactant flow into the inlet is reduced or stopped when non-target components are present at the outlet as they elute, to avoid unwanted reaction with such components.

At least one of the types of processing preferably comprises detection of the eluate. The present invention, for example, can enable enhanced detection of samples and thus improved assay performance from a chromatography column. In various embodiments the invention may enable, for example, a higher detection specificity, a lower limit of detection for species being chromatographed due to improved detection sensitivity, an improved signal to noise ratio through a lower noise level and/or improved peak resolution within a chromatographic assay. The invention may enable a simultaneous detection of both unreacted and reacted eluate by the use of multiple ports on the column outlet which remove the unreacted and reacted eluate in separate flow streams. In this way, differences between native (unreacted) eluate and reacted eluate can be observed and changes in the system can be gauged.

With regard to preparative reaction chromatography, synthesis or catalysis, the invention may enable the collection of purer fractions of reacted samples with improved specificity and yield of reactions.

These and other advantages will be described in more detail and become more apparent from the following description of the invention.

The invention could be applied in the following areas, amongst others: biodetection in natural products; amino acid analysis; analyses involving enzyme digestions; chemical synthesis; automated nanoscale synthesis; low volume organics; and chiral selective synthesis.

The invention avoids the need for separate reaction equipment downstream of the column by providing that reactions occur directly at the column outlet. The invention can be seen as a combination of chromatographic separation and pre- or post-column modification in one unit. The combination of separation and modification eliminates the need for extra equipment, time and labour as well as facilitating automation of the post-chromatographic (e.g. post-HPLC) modification process.

The present invention can be used in numerous configurations. For example, for multistage processes, the column according to the present invention can be sequentially linked with reaction intermediate zones. Separation and synthesis can be undertaken for complex processes on small scales. The detection of products can be hyphenated or linked seamlessly to separation. The methods provided by the invention are also scalable to process systems.

Preferably, the invention is implemented by providing the column outlet with a flow distributor that allows in-flow of reactant to the eluate and allows out-flow of reacted eluate product. The flow distributor is preferably the means by which the eluate leaves the column via one or more fluid ports. In some embodiments, advantageously, the flow distributor further allows simultaneous out-flow of a separate portion of eluate, for example, that is unreacted or reacted differently to the first portion. The flow distributor is preferably in the form of an end fitting that fits to the outlet end of the column. The end fitting is accordance with the present invention may simply take the place of the standard single port end fitting fitted to the outlet of, for example, conventional HPLC columns.

The flow distributor preferably enables a fluid flow in and out of a peripheral region of the column (e.g. reactant in and product out) and a fluid flow out of a central region of the column (e.g. unreacted eluate out).

The flow distributor preferably reacts eluate emanating from a defined or restricted region of the column, especially a restricted radial region of the column. This has been found to exhibit a greater degree of chromatographic resolution of components compared to eluate emanating from across the full radial dimension (width) of the column. Further details of the flow distributor are described below.

The mixing of reactant and eluate and reaction preferably begins to take place at least partially in a reaction zone in the outlet, which more preferably is within the flow distributor. The mixing and reaction may continue downstream of the reaction zone and flow distributor. The intimate nature of the eluate and reactant mixing in the flow distributor can enhance reaction efficiency. The reaction zone in the flow distributor is preferably adjacent or in contact with a frit in the outlet and/or more preferably is on the downstream side thereof, i.e. the reaction more preferably begins and takes place after the eluate has passed through the outlet frit. Thus, reactant is preferably flowed into the eluate flow through each reactant port whereby the reactant and eluate mix in a reaction zone that is adjacent or in contact with the frit.

In addition to the reaction zone described, in some embodiments where an additional, separate portion of eluate from the first reacted portion is also extracted from the outlet, there is preferably at least one other zone, e.g. within the flow distributor. The other zone may be a zone for unreacted eluate or another reaction zone (i.e. a second reaction zone) in which another reactant is introduced for another reaction to begin and at least partially take place. Thus, two reactions could take place simultaneously. The other zone(s) are likewise also preferably adjacent or in contact with the frit. Preferably, each zone is in contact with its own section or sections of the frit where these sections are different from sections of the frit that are in contact with a different zone.

The reaction zone is preferably fluidly separate from the at least one other zone, i.e. is preferably fluidly separate from at least one other portion of eluate (e.g. unreacted or differently reacted eluate). The reaction zone in contact with the frit may be kept fluidly separate from the other zone(s) or portion(s) of eluate by a non-porous barrier between sections of frit, each zone or portion of eluate being in fluid communication with the column bed through its own respective section of frit.

The reacted eluate and the reaction zone are preferably provided fluidly separate from a further portion of eluate and further zones. The further portion may be unreacted eluate or another reacted eluate that is reacted differently to the first reacted eluate. In some embodiments, therefore, there are two or more fluidly separate reaction zones, each being supplied with its respective reactant. Each reaction zone is fed with its own reactant via its own one or more reactant ports and has its reacted eluate received by its own one or more product ports for sending to the downstream processing.

The eluate is preferably split and delivered from the column bed into the reaction zone and at least one other zone via a split or segmented frit at the outlet, i.e. a frit having two or more separate frit sections, fluidly separate from each other (e.g. by a non-porous barrier). A preferred split frit comprises a central frit section fluidly separated from an outer frit section (or sections) surrounding the central frit section in an annulus (or split annulus) shape. The reaction zone may be in contact with one of these frit sections, e.g. an outer or annular section, and another zone (for unreacted or differently reacted eluate) may be in contact with another frit section, e.g. central frit section.

The split frit may be provided as three or more sections, e.g. a central section and two fluidly separate outer sections, e.g. with each outer section configured substantially as a half annulus or semi circle around the central section. This may provide that at least two reaction zones are present, as well as a zone for unreacted eluate, each zone in contact with a respective separate frit section (e.g. the reaction zones adjacent or in contact with the outer sections and the zone for unreacted eluate adjacent or in contact with the central section). Such arrangements may enable multiplexed reactions to take place, i.e. simultaneous reactions within the same apparatus.

Further details of split frits are described below. Further details of split frits and flow distributors which may be utilised in the present invention are also described in the following co-pending patent applications filed by the applicants: GB application no. 1108861.4; GB application no. 1108859.8; U.S. Ser. No. 61/519,731 and U.S. Ser. No. 61/519,733, all filed on 26 May 2011. The contents of these patent applications are hereby incorporated by reference in their entirety.

Herein, reaction of the reactant flow with the eluate flow means reaction between at least one reactant species in the reactant flow with at least one sample component in the eluate.

The reactant may comprise a single reactant species (single chemical entity) or two or more reactant species (two more chemical entities). The term reactant herein encompasses a catalyst as a possible reactant species. Examples of the reactant can include DPPH (2,2-diphenyl-1-picrylhydrazyl radical) reagent for antioxidants to improve detection, or enzymes for protein digestion Where there are two or more reactant ports, each reactant port may introduce a reactant which is the same as or different to the reactant introduced by another reactant port.

The apparatus comprises a chromatography column, which is typically a liquid chromatography column but may be a supercritical fluid chromatography column, the column having an inlet and an outlet, whereby a mobile phase containing a solvent and sample to be separated may be introduced to the column through the inlet and flowed longitudinally (i.e. axially) along the column to the outlet.

The outlet is configured to feed reactant into the flow of eluate (i.e. mobile phase leaving the column). The outlet in certain preferred embodiments is configured such that the eluate flow is split into at least two separate portions, wherein at least one portion is then reacted with the reactant to produce a reacted eluate and, optionally, at least one portion may be left unreacted. Each portion is preferably processed separately, e.g. directed to its own processing means separate to processing means which the other portion (or portions) is (or are) directed to. In certain preferred embodiments, one portion of the eluate flow leaving the column is maintained separately from another portion and detected separately to the other portion. In certain preferred embodiments, each portion is detected separately by its own separate detector. In respect of preparative reaction chromatography, a portion of reacted eluate flow leaving the column may be maintained separately from another, unreacted portion and fractions of the reacted portion may be collected separately from the other portion.

In one variant of the invention, a first portion of the flow of eluate, preferably a reacted portion, is directed to a first processing unit and a second portion of the flow of eluate, preferably an unreacted portion, is directed to a second processing unit separate from, and preferably different to, the first processing unit. For example, preferably the first processing unit for the reacted portion comprises a detector, e.g. for detecting a reaction product, and the second processing unit for the unreacted portion may comprise a detector (of the same or a different type), waste receiver, or more preferably may be the inlet of the same or another chromatography column so that the unreacted portion may be subjected to at least a further round of chromatography. After such a further round of chromatography, preferably using the same or another chromatography column with an outlet according to the present invention, the further chromatographed unreacted eluate may be reacted and detected. However, in some embodiments, the second processing unit may also comprise a detector for detecting the unreacted sample present in the unreacted eluate.

The reaction product may be only an intermediate, in which case, the subsequent processing for that reaction product may comprise one or more subsequent reactions. The one or more subsequent reactions may each take place in another column outlet according to the invention (i.e. combined with chromatographic separation) or in a separate reactor.

Many other processing units, and combinations thereof, could be employed and these are discussed in more detail herein below. In this way, for example, the invention provides a column with an outlet configured to selectively direct a portion of the eluate flow to a first processing unit, e.g. a detector, while it directs another portion to another processing unit separate to the first processing unit, at least one portion having been reacted in the outlet.

Preferably, where both reacted and unreacted eluate flows leave the column, the reacted eluate emanates from a different region of the column cross section to the unreacted eluate, e.g. the unreacted eluate may emanate from a first region and the reacted eluate may emanate from a second region of the column, these regions thus corresponding to different regions of a packed bed in the column. More preferably, such separate reacted and unreacted portions of eluate emanate from different radial regions of the column, e.g. the unreacted eluate may emanate from a first radial region and the reacted eluate may emanate from a second radial region of the column, different from the first radial region. The term radial region herein means a region in the transverse cross-section or plane of the column, i.e. the cross-section or plane perpendicular to the central or longitudinal axis of the column. The terms radial or radially herein thus refer to a direction perpendicular to the central or longitudinal axis of the column.

Preferably, the first region of the column is a radial region located substantially away from the walls of the column. Preferably, the column is a packed column having a column bed therein and a first region of the packed column is a radial region substantially away from the walls of the column and from which unreacted eluate leaves the column. Still more preferably, the unreacted eluate emanates from a central radial region of the column and the reacted eluate emanates from a radial region located radially outward of the central radial region (a peripheral region). Most preferably, the central radial region of the column is a region located substantially on a central axis running longitudinally through the column from the inlet to the outlet. In this way, a central core of the eluate flow can be directed as one portion to a detector, or other processing unit, while a remainder of the eluate flow, e.g. as a peripheral eluate flow surrounding the central core of eluate flow, is reacted and directed elsewhere, e.g. to one or more different processing units (typically also a detector or fraction collector).

Preferably, the reactant port or ports peripherally surround the central axis of the column. Preferably, the product port or ports surround the central axis of the column. A central port is preferably located on the central axis of the column, which may direct unreacted eluate. In some embodiments, the central port may be used as a reactant or product port.

In some embodiments, the outlet is arranged to split the flow of eluate as it leaves the column into more than two portions. For example, the outlet in such embodiments may be arranged to split the flow of eluate as it leaves the column into three or more separate portions, each portion being directed to a separate processing unit than the other portions, i.e. so there are three or more separate processing units. At least one of the portions of eluate is reacted in accordance with the invention. Two (or more) of the portions of eluate may be reacted. One of the portions may be unreacted eluate. The two (or more) portions of reacted eluate may be reacted with different reactants to each other. Thus, different reactions may be performed simultaneously on the eluate, i.e. multiplexing of reactions may be achieved.

Some discussion of the migration of a sample through a typical packed column is now given as background to aid further understanding of the present invention. The concentration in a moving sample band within a packed column decreases as the distance from the column central axis is increased, due partly to uneven flow within and across the column diameter and partly due to diffusion and related mass transfer effects associated with transport within and around a packed bed whose own density and homogeneity can vary with the effectiveness with which the column is filled. The moving sample band also tends to have a parabolic shape. These phenomena can lead to drawbacks with sample separation efficiency, detection and resolution since a conventional column outlet gathers eluate from across the whole diameter of the column. The present invention, however, enables the flow of eluate exiting the column to be split or segmented, e.g. depending on where it emanates from across the column diameter, so that a portion of the eluate flow is separated from at least another portion and the portions can be reacted or not separately (independently) and then processed separately.

A detector suitable as a type of processing unit may be selected from the following (without limitation thereto): a mass spectrometer (MS) system, a UV detector, a fluorescence detector, chemiluminescence detector, and a decolorisation detector such as various biodetector, for example such as the DPPH antioxidant detector. Some biodetectors, such as the DPPH antioxidant detector, require reagents to enter the eluate stream. Maximum sensitivity is dictated by the ratio of mobile phase to DPPH reagent. Being able to split the flow exiting the column beneficially reduces the consumption of DPPH reagent, without loss in sensitivity. The processing preferably comprises detecting changes in the reactant and/or eluate as a result of the reaction that takes place. Multiple detection devices can also be employed, simultaneously, with minimal dead volume. These detectors can be sample destructive since a portion of the unreacted sample can still be used for further processing.

The ratio of the respective volumes of the different portions of eluate flow may vary, thus the degree of flow segmentation may be tunable. The optimum flow ratio is typically dependent upon the particular process being conducted. Thus, the amount of flow from a peripheral column region e.g. to be reacted, versus that from a central column region may be varied.

The ratio of peripheral and central eluate flows may be varied by various means as described in more detail below. Preferably, the portion of eluate which is reacted, and processed separately, is 70% or more (by volume), or 50% or more, or 30% or more of the total eluate. For example, the reacted eluate portion may be 50% or more, 45% or more, 40% or more, 35% or more, 30% or more, 25% or more, 20% or more, 15% or more, 10% or more, or 5% or more of the total eluate. This reacted portion is preferably a portion which emanates from a peripheral column region (i.e. radially surrounding the central column region).

The ratio of the respective volumes of the different portions of eluate flow may be varied by selecting the ratio of the areas of different frit sections as described below and/or by selecting the number and/or size of the outlet ports. The ratio of the respective volumes of the portions of eluate flow from the outlet (degree of segmentation) may be varied by adjusting the pressures and/or flow rates in one or more of the reactant flow, product eluate flow and any unreacted eluate flow, e.g., by means of a pressure or flow regulator in a channel carrying the flow and/or, e.g., by varying the length or diameter of tubing downstream of the outlet ports.

The column outlet is preferably provided with a frit, wherein the frit is located such that the eluate leaving the column flows through the frit. Preferably, the frit is located within the internal diameter of the column at the outlet. The frit may comprise one or more frit sections as hereafter described.

The outlet frit preferably is in a frit assembly configured to split or divide the flow of eluate as it leaves the column into at least two separate portions. The configuration of the frit in this way enables separation of the eluate flow to be performed on-column, not post-column. In order to split the flow, preferably the outlet frit assembly is a split frit assembly (also termed herein segmented frit assembly) which comprises at least two separate frit sections, that are separated from one another by one or more flow barriers, e.g. a non-porous body may provide a flow barrier, or a non-porous coating may provide a flow barrier, e.g. wherein such coating is provided on one or more surfaces of at least one of the separate frit sections, which one or more coated surfaces abut the other frit section or sections. The flow barrier prevents lateral, i.e. radial, flow of eluate between the frit sections as the eluate passes through the frit assembly thereby enabling flow segregation into separate portions. Thus, the eluate flowing through one or more first frit sections may provide the first portion of flow which may be reacted with reactant and the eluate flowing through one or more second frit sections may provide the second portion of flow, which may remain unreacted or be reacted differently to the first portion, since the eluate flowing through the first frit section(s) is fluidly separate or isolated from the eluate flowing through the second frit section(s) by virtue of the fluid barrier e.g. in the form of the non-porous body. In such cases, preferably, the one or more first frit sections are in communication with one or more first reactant ports in turn in communication with one or more first reactant sources and the one or more second frit sections are in communication with one or more second reactant ports in communication with one or more second reactant sources. The one or more first frit sections are also preferably in communication with one or more first product ports and one or more second frit sections are in communication with one or more second product ports. In a preferred such embodiment, which allows multiplexed reactions, a first frit section communicates with both a first reactant port and a first product port; and a second frit section communicates with both a second reactant port and a second product port.

Since the sections of the split frit occupy different regions, especially different radial regions, of the column, the split frit determines that at least two separate portions of eluate emanate from different regions of the column, preferably different radial regions as described. On the other hand a conventional, single frit piece is less efficient because the flow of eluate through the frit is less ordered and therefore eluate which has flowed through different regions of the column bed may become mixed to an undesirable degree as it flows through the frit. The split frit on the other hand is arranged to ensure there is no cross flow between the different sections of the frit. The use of a split frit enables the eluate that has flowed through different regions of the column bed to exit the frit in different portions which correspond to the different regions of the column.

A preferred configuration of split frit assembly comprises at least one centre frit section, a non-porous body surrounding the at least one centre frit section and at least one outer frit section surrounding the at least one centre frit section but being separated therefrom by the non-porous body. More preferably, the split frit comprises a radially central centre frit section, a non-porous body annularly surrounding the centre frit section and an outer frit section annularly surrounding the non-porous body and thus the centre frit section. This arrangement of a central frit section annularly surrounded by an outer frit section is termed herein an annular split frit.

Most preferably, the radially central centre frit section is located substantially on the central axis running longitudinally through the column from the inlet to the outlet. Such split frit configurations at the outlet permit the central frit section(s) to produce a portion of flow emanating from a central radial region of the column and the outer frit section(s) to produce a portion of flow emanating from a radial region located radially outward (peripherally) of the central radial region.

In a further embodiment, the outer frit section is divided into preferably two frit sections, or optionally more than two frit sections, that are fluidly separated or isolated from each other and from the central frit section where used. In this way, eluate flow through each of the outer frit sections can be fluidly separated from the other, and each such separate eluate flow may be reacted independently of the other. This permits multiplexed reactions of the eluate to take place.

The centre frit section and outer frit section may be of various relative areas thereby splitting the eluate flow into portions from central and peripheral regions of different relative area. The ratio of the areas of the frit sections may thereby be a means to vary the ratio of the respective volumes of the split portions of eluate flow. For example, the ratio of the area of the outer frit section to the area of the central frit section may vary, e.g. from 90%:10% to 50%:50%, more typically from 80%:20% to 50%:50% but ratios outside these ranges may also be used. A preferred ratio of the area of the outer frit section to the area of the central frit section is from about 6:1 to about 1:1, more preferably from about 3:1 to about 1:1, still more preferably from about 2.5:1 to about 1.5:1, and most preferably about 2:1.

The frit sections may have the same or a different density. For example, the central frit section may have a different density to the outer frit section. In one type of embodiment, the central frit section may have a lower density than the outer frit section. Thus, eluate may be controlled to flow preferentially through a frit section of lower density relative to a frit section of higher density.

The outlet frit assembly typically comprises an outer non-porous fitting, preferably made of polymer, which e.g. fits to the outlet end of the column so that the frit assembly forms a frit cap. Such an outer fitting is preferred because for example a steel frit will not seal well against a steel column wall. The polymer fitting may be made of various polymers, e.g. PTFE (Polytetrafluoroethylene), ETFE (Ethylene tetrafluoroethylene), PEEK (Polyetheretherketone) or KEL-F® (Polychlorotrifluoro-ethylene), more preferably PEEK. In general, any non-porous parts of the frit assembly may be made of plastics or polymer, e.g. PTFE, ETFE, PEEK or KEL-F®, more preferably PEEK.

The outlet frit assembly in some other embodiments may comprise a single piece of porous frit, i.e. rather than sections of frit. The single piece of porous frit may, as in the other described embodiments, be held in an outer non-porous, preferably polymer, fitting, which e.g. fits to the outlet of the column so that the frit assembly forms a frit cap.

The outer non-porous fitting of the outlet frit assembly may have apertures to separate the flow of eluate. For example, the outer non-porous fitting may have a radially central aperture to allow through flow of a portion of eluate from the frit that emanates from a radially central region of the column, and may have one or more peripheral apertures radially outward of the central aperture to allow through flow of a portion of eluate from the frit which emanates from a peripheral radial region of the column (surrounding the radially central region). The portion of flow that emanates from the peripheral region of the column may be gathered from the outer sides of the frit, e.g. by having one or more peripheral apertures in the side walls of the outer non-porous fitting.

The outlet frit assembly is preferably of circular outer shape to fit a circular cross section column, although frit assemblies of other shapes may be used depending on the column shape for example.

The material of the outlet frit may be conventional frit material as used in liquid chromatography, e.g. steel. Thus, the frit may simply be configured in the split manner described herein to split the eluate flow that flows through it. For example, the frit material, thickness (depth), and porosity may be conventional as used in LC systems. For example, a frit of typical thickness of 0.25 to 2 mm may be used. For example, a frit with nominal 2 µm porosity may be used. However, frits of other porosities can be used, e.g. in the range nominally of 0.1-20 µm. The non-porous body of the split frit embodiments is preferably made of a plastics or polymer, e.g. PTFE, ETFE, PEEK or KEL-F®, more preferably PEEK but may be made of metal, e.g. stainless steel. Such non-porous materials may also be provided as a thin layer or coating on one or more surfaces of one or more frit sections that abut another frit section to provide a flow barrier. The non-porous flow barrier alternatively could be made of a metal. Such a metal barrier could be formed by sputtering as a thin layer or coating on one or more surfaces of one or more frit sections that abut another frit section. Such thin layer or coating flow barriers may have an advantage of low drag on the eluate flow.

The width (i.e. measured in the radial direction) of the flow barrier or non-porous body is preferably small compared to the width of the frit sections, i.e. is preferably lower than the width of each of the frit sections. It is preferably as small as possible, ideally micron sized. Thus, any possible drag on the flow of separated components that may be caused by the presence of the flow barrier in the eluate flow, or any dead zone effects behind the flow barrier, which may thereby be minimised. It will be appreciated, however, that the barrier should not be so thin that segregation of the flow into separate portions is not effectively achieved.

Preferably, the column inlet and outlet are each located at an end of the column, i.e. at opposite ends of the column. The column in use preferably has a flow distributor at its outlet end (outlet flow distributor). The outlet flow distributor is preferably configured to convey through separate fluid ports therein the reactant flow(s) into the eluate and the reacted eluate flow(s) and optionally any portion(s) of unreacted eluate. The fluid ports of the flow distributor are thus the reactant port(s) and product port(s), as well as any additional port(s). The flow distributor is thus effectively a distributor for the eluate flow and reactant flow.

The outlet flow distributor may be provided as a column end fitting, i.e. a detachable end fitting which is releasably fitted to the column outlet end in use. Alternatively, the outlet flow distributor may be made integral with the end of the column. A preferred arrangement is to have the outlet flow distributor as a separate end fitting part that is fitted to the end of the column in use. However, it will be appreciated that in other embodiments it is possible that the flow distributor be made integrally with the column. In such integral embodiments, the flow distributor is not a separate part. Herein, although the preferred embodiment of a separate end fitting will be primarily used to illustrate the flow distributor, the features of such an end fitting generally also apply to the case where the flow distributor is made integrally with the column end.

The flow distributor at the outlet is configured to have a plurality of ports to separately convey the separate reactant flow(s), reacted eluate flow(s) and any unreacted eluate flow(s), e.g. where the eluate flows may have been split at the outlet, such as by the split frit assembly described. These plurality of ports comprise the one or more reactant ports, the one or more product ports and any additional port(s) (e.g. for unreacted eluate).

In some embodiments, the flow distributor alone may be arranged to split the eluate flow into the separate portions, e.g. where a standard (non-split) frit is used at the outlet. The flow distributor thus has a plurality of separate ports, comprising at least reactant and product ports and optionally unreacted eluate port(s). The eluate may thereby be separated into separate portions which are distributed to different processing units. As described above, the flow distributor is preferably provided as an end fitting, wherein the end fitting includes the plurality of separate ports.

The one or more reactant ports of the outlet flow distributor, e.g. end fitting, preferably are arranged to convey reactant into at least a portion of the eluate flow. The one or more product ports of the outlet flow distributor are arranged to convey the reacted eluate to one or more processing units. Another port or ports of the outlet flow distributor may be arranged to convey another portion of eluate flow, e.g. split from the first portion of eluate by the use of a split frit as described, to a separate processing unit. The portions of eluate flow may emanate from different regions of the column, more preferably different radial regions of the column as described.

The separate ports of the flow distributor may comprise a first set of at least one port which is located in the distributor so that in use it is aligned with a first region, preferably first radial region, of the column. For example, in the case of a flow distributor which is in the form of an end fitting, the first set of at least one port of the end fitting is located in the fitting such that when it is fitted to the outlet end of the column the first set is aligned with a first region, preferably first radial region, of the column. The first radial region is preferably the central radial region of the column, more preferably located substantially on a central axis running longitudinally through the column, and a first set of at least one port is herein termed a central port set in that case. In some embodiments, the first or central port set may be for conveying a portion of the eluate flow, which may be unreacted eluate or reacted eluate flow, preferably unreacted eluate. In a separate embodiment, the first or central port set may convey a reactant flow into the eluate in the outlet. The first set of at least one port (e.g. central port set) is preferably radially aligned with a central frit section of a split frit assembly, where a split frit assembly is employed. The port(s) of the first or central port set may be independently closeable or flow restricted, e.g. so that when a port is not required, for instance if an unreacted eluate flow is not required, then it may be closed or restricted. The port(s) may be so closeable by being attachable to a blank fitting or cap, or by having a switchable flow valve fluidly connected thereto.

The separate ports of the outlet flow distributor may comprise a second set of at least one port (preferably a plurality of ports) which is located in the distributor so that in use it is aligned with a second region, preferably second radial region, of the column. For example, in the case of an end which is in the form of an end fitting, the second set of at least one port (preferably a plurality of ports) of the end fitting is located in the fitting such that when it is fitted to the outlet end of the column the second set of at least one ports is aligned with in a second region, preferably second radial region, of the column. The second radial region is preferably a radial region located radially outward or peripherally of the central radial region and a second set of at least one port is herein termed an outer or peripheral port set in that case. In some embodiments, one or more ports of the second or outer port set are for conveying a portion of the eluate flow, preferably a reacted eluate flow, and are the product ports in that case. In some embodiments, one or more ports of the second or outer port set are for conveying a reactant flow and are the reactant ports. The second set of at least one port (e.g. outer or peripheral port set) is preferably radially aligned with an outer or peripheral frit section of a split frit assembly, where a split frit assembly is employed. One or more of the second or outer port set may be closeable or flow restricted, e.g. so that when it is not required, for instance if reactant flow through that port is not required, then it may be closed or restricted. The port(s) may be so closeable by being attachable to a blank fitting or by having a switchable flow valve fluidly connected thereto.

A third set and optionally further sets of port(s) may be included in the flow distributor in other embodiments, e.g. where third and optionally further portions of eluate are separated for processing.

In preferred embodiments, the first port set for directing a first portion of the eluate comprises a radially central port and the second set comprises a plurality of outer peripheral ports radially outward of the central port. However, it will be appreciated that in some embodiments the first set may comprise a plurality of central ports, i.e. in a central radial region, and a plurality of outer peripheral ports radially outward of the first set of ports.

Preferably, the flow distributor is arranged very close to or, most preferably, in contact with the frit assembly such that the portions of eluate which have passed through the frit assembly (especially the split frit) having emanated from different radial regions of the column bed pass to the respective sets of ports in the distributor, e.g. first and second portions of eluate which have passed through the frit assembly pass respectively into first and second sets of ports in the flow distributor. By arranging the flow distributor in direct contact with the frit assembly it is less likely to introduce voids. The flow distributor in use may sit flush against the frit surface. The flow distributor in use may sit in contact with one or more of the non-porous parts of the frit assembly so that the one or more non-porous parts provide a seal between the frit (e.g. frit sections) and flow distributor thereby sealing adjacent portions of eluate flow from each other. For example, the non-porous outer frit fitting and/or non-porous flow barrier (which separates the porous frit sections), may seal against the flow distributor to thereby keep the portions of eluate that have passed through respective frit sections separate. Between each of the frit section(s) and the port(s) aligned with those frit sections there is preferably a volume, typically very small volume, for example to allow reactant and eluate to mix and react. Such volumes are preferably fluidly sealed by the non-porous parts of the split frit assembly. One such volume is the reaction zone in which reaction at least partially occurs. One or more other such volumes are the further zones, in which other portions of eluate may either be reacted or not. The one or more reactant ports and one or more product ports are preferably in fluid communication with each other via such a volume (reaction zone).

The ports of the outlet flow distributor, preferably end fitting, preferably each are in fluid communication with connected exit plumbing to carry eluate, e.g. to the processing unit(s).

Preferably, the outer or peripheral ports are arranged symmetrically about the central axis of the column. For example, the outer or peripheral ports may be equally spaced apart and/or equidistant from the central port. However, the outer or peripheral ports could be arranged un-symmetrically.

Preferably, the outlet flow distributor comprises one central port and from 2 to 12 outer ports, i.e. 2, 3, 4, 5, 6, 7, 8, 9, 10, 11, or 12 outer ports, more preferably one central port and from 3 to 6 outer ports. An outlet flow distributor having 3, 4, 5 or 6 outer ports is a good example. However, these numbers are not limiting on the invention.

As preferred examples, in a first preferred embodiment, the outlet flow distributor, preferably end fitting, comprises one central port and three outer ports (i.e. a four port configuration). In a second preferred embodiment, the flow distributor comprises one central port and six outer ports (i.e. a seven port configuration). The number of ports can be varied, e.g. four port, five port, six port, seven port, eight port, nine port, ten port, eleven port, or twelve port configurations may be used, or indeed configurations with even higher numbers of ports may be used.

With regard to the number of central ports versus the number of peripheral ports, the outlet flow distributor, preferably end fitting, in the above-mentioned preferred embodiment may have one central port at the centre, preferably for unreacted eluate flow, and three peripheral ports surrounding it (preferably comprising at least one reactant port and at least one product port) but it should be understood that the present invention contemplates any number of peripheral ports, e.g. one or more peripheral ports. The present invention does not exclude the possibility that reacted product could also exit from the central port. Preferred examples may have from 3 to 12, more preferably 3 to 10, peripheral ports, particularly 3, 4, 5, 6, 7 or 8 peripheral ports. A flow distributor, preferably end fitting, with 3, 4, 5 or 6 peripheral ports is a good example. Furthermore, the present invention contemplates any number of central ports (i.e. those ports which transmit a flow of eluate from a central radial region), e.g. one or more central ports. Preferably, there is one central port.

The ports in general may be located in the end or sides of the body of the flow distributor, preferably the end. The peripheral port or ports may be located in the end or sides of the flow distributor. The central port or ports may be located in the end or sides of the flow distributor but preferably the end. In some embodiments, the portion of flow that emanates from the peripheral region of the column may be gathered from the outer sides of the frit and e.g. directed through the peripheral port or ports located in the sides of the flow distributor. The portion of flow that emanates from the central region of the column may be gathered from the centre of the frit and e.g. directed through a central port or ports located in the end of the flow distributor.

Selecting the number and the size of the port(s) channeling each portion of the eluate may be a means to vary the ratio of the respective volumes of the portions of eluate flow (i.e. the degree of segmentation of the eluate). The ratio of the respective volumes of the portions of eluate flow from the outlet (degree of segmentation) may alternatively or also be varied by adjusting the pressures in the downstream channels following the ports (i.e. the differential outlet pressure). The differential outlet pressure may be varied, e.g., by varying the lengths of tubing or diameter of tubing following the ports.

In use, one or more of the ports may be closed, i.e. blocked off, so that eluate does not flow therethrough but instead is caused to flow through the remaining open ports. Such port(s) may be opened when the port(s) is/are required to be used.

A portion of the flow of eluate referred to herein comprises all eluate which is gathered and sent to a particular processing unit by a particular route. A portion of eluate may thus comprise eluate that has been gathered from one or more ports, e.g. a plurality of peripheral (product) ports, of the flow distributor and collectively sent to a particular processing unit, i.e. for combined processing.

The outlet end fitting may be of similar external dimensions to a conventional end fitting. In this way, bulky reaction equipment is avoided. The end fitting may be either hand tightened or tightened with the aid of a tool if necessary to the end of the column at the column outlet. The outlet end fitting is preferably fitted to the outlet end of the column by a screw connection, or may be push fitted, or may connect using another type of connection. As with many conventional types of end fittings for analytical columns, e.g. for HPLC, a typical connection for the end fitting on the column comprises an external screw thread on the outlet end of the column and an internal screw thread inside the end fitting. In such arrangements, the end fitting thus screws onto the end of the column and covers the outlet. In other embodiments, the outlet end fitting may be fitted internally in the column end, e.g. with certain types of self-packed columns and axial compression columns. In such embodiments, the end fitting may be push (friction) fitted into the column end and optionally may carry a sealing means, such as one or more sealing rings or o-rings, on its outer surface to seal against the internal surface of the column wall. The outlet end fitting may be made of any suitable material. The end fitting may be made of metal, preferably stainless steel, especially where it is fitted to a metal column, e.g. stainless steel column, preferably by a screw thread or by using a SWAGELOK® type fitting. In other cases, e.g. where the column is glass, the end fitting may be made from other suitable materials, e.g. plastics, for instance PEEK. It will be appreciated that separation of the eluate flow is preferably performed on-column, and not post-column as is the conventional method. This is achieved by the features of the invention described herein, such as the split frit assembly and flow distributor.

The column outlet may split the eluate flow leaving the column into more than two portions, e.g. three, four or more portions. Preferably, the outlet splits the eluate flow into two portions, e.g. one which is reacted and one which is not, which provides a simple, low cost, elegant and advantageous embodiment of the invention as illustrated in more detail herein below. In another embodiment, the outlet only flows out a reacted eluate and no other eluate portion.

The split portions of eluate leaving the outlet may be further directed, i.e. downstream of the flow distributor, by eluate directing means to the processing unit(s). Preferably, the eluate directing means for directing the portion(s) of the eluate to the processing unit(s) receives the flow of eluate from the flow distributor, and typically comprises a plurality of conduits, e.g. tubing. Each port of the flow distributor through which eluate or reactant is flowed in use preferably has a conduit attached thereto. Preferably, where present, the at least two separate portions of eluate are directed in separate channels or conduits to their respective separate processing means. Suitable tubing for this purpose may comprise any standard or conventional tubing for use in liquid chromatography, e.g. plastics tubing (preferably PEEK tubing), or metal tubing (preferably steel tubing). Each portion of eluate flow is preferably directed through its own set of one or more conduits to a respective processing means.

Preferably, the inlet and outlet are each located at an end of the column, i.e. the inlet and outlet are located at opposite ends of the column. The inlet is configured to introduce a flow of mobile phase into the column carrying a sample, whereby the sample separates into components as it advances longitudinally through the column from the inlet to the outlet carried by the mobile phase. The inlet may be a conventional inlet for column chromatography. A frit may be used in the column at the inlet as for many types of conventional chromatography. In other words, the invention may be implemented by making modifications as described herein only at the outlet end of the column. The sample may, for example, be introduced into the column at the inlet across the width of the column, either via single inlet port or via multiple inlet ports (such as an inlet or head flow distributor having multiple inlet ports spaced across the width of the column to more evenly distribute flow across the column width) or at a restricted radial region of the column, e.g. by central point injection (CPI), or at a restricted radial region of the column using a curtain flow process that is achieved by employing a split flow or segmented flow fitting (similar to the outlet end fitting described herein), at the column inlet. In such cases, the sample may thereby be introduced preferentially (i.e. in relatively larger amount) via one or more of the ports, with other ports introducing less or no sample in the mobile phase. The portion of mobile phase introduced with sample preferentially contained therein may thus flow through the column in a radially restricted manner bounded by the portion of mobile phase introduced containing less or no sample.

Typically, the flow of mobile phase containing sample is introduced into the column at the inlet in one portion. Typically, the mobile phase containing sample is introduced into the column through a single inlet fluid port, or through multiple inlet fluid ports, but in one portion of one composition.

The inlet is preferably provided with an inlet frit, wherein the frit is located such that the mobile phase entering the column flows through the frit. Preferably, the inlet frit is located within the internal diameter of the column at the inlet.

In certain embodiments, the inlet may be configured to introduce the flow of mobile phase into the column in at least two separate portions which are independently controllable, and may be configured to introduce the portions into different radial regions of the column, such that the portions flow longitudinally through the column in different radial regions. Preferably, the sample concentrations in each portion or the flow velocity of each portion or both are independently controllable. The composition of the mobile phase portions may be controllable. Thereby, the mobile phase portions may be of the same or different composition, e.g. have the same or different solvents and/or have the same or different samples. One portion, e.g. a radially peripheral portion, may even be a non-solvent or at least a solvent having lower solubility for the sample to be separated (e.g. water), thereby promoting the containment of sample in the other, e.g. radially central, portion.

The outlet is preferably configured such that the portions of mobile phase that have been flowed through the column in different regions by means of the segmented inlet are split from each other at the outlet to provide the separate portions of eluate.

The invention in such embodiments thus allows a sample to be introduced to the inlet of the column preferentially contained within one of the portions of mobile phase and that portion to be introduced to and flow through a restricted radial region, preferably the central region, of the column. Such a portion is herein also termed the sample flow. A so-called curtain flow may then be provided by one or more of the other portions of mobile phase, preferably flowing through the wall or peripheral region of the column (annularly surrounding the central region), which restricts the transverse migration (i.e. diffusion) of the sample, e.g. migration to the wall. In certain embodiments, the curtain flow is in the form of an annular band of mobile phase which flows around the sample flow that is in the form of a central band of mobile phase. In a further advantage of such embodiments, the linear flow velocities of the different mobile phase portions can be controlled. The flow velocities can be controlled either by using separate pumps for the portions (a separate pump for each portion), or by other means, for example by placing flow restrictors in the tubing carrying each portion (i.e. to provide differential pressure between the tubing carrying each portion, for example between peripheral fluid lines and a central fluid line).

The flow velocities may be arranged to be substantially the same. In a conventional column with a single inlet port, the central or sample flow is focused on the central region of the column bed, in which flow speeds are naturally higher anyway. This leads to a bowl shaped sample band, with faster moving sample in the central region and slower moving sample in the peripheral or wall region. In certain embodiments, the invention can overcome or reduce this deficiency by arranging for separate flows of different mobile phase portions, such as a central flowing portion and an additional peripheral flowing portion, in which their flow velocities can be arranged to be substantially the same, thereby providing a flow velocity profile in the transverse cross section which is substantially flat or at least significantly flatter than in the conventional case. Flat flow profiles can deliver peaks to the outlet in a narrower band of time (i.e. narrower peak widths in the chromatogram) and thus improve resolution.

A flow distributor similar to the outlet flow distributor described could be utilised at the column inlet in certain embodiments. Such a flow distributor, especially in combination with a split frit at the inlet, could thus provide a segmented inlet in which mobile phase is introduced into the column in different radial regions as described. The ports of an inlet flow distributor could be used as one or more reactant ports to flow in reactant and one or more mobile phase ports to flow in mobile phase containing sample at the inlet. Optionally, the reactant could thereby be fed to mobile phase portions restricted to certain radial regions of the column in a segmented inlet configuration.

The segmented inlet configuration preferably utilises an inlet frit assembly configured to separate the flow of mobile phase as it enters the column into at least two separate portions. In order to split the flow, preferably the inlet frit assembly is a split frit assembly (also termed herein segmented frit assembly) which comprises at least two separate frit sections, that are separated from one another by one or more flow barriers, e.g. a non-porous body may provide a flow barrier, or a non-porous coating may provide a flow barrier, e.g. wherein such coating is provided on one or more surfaces of at least one of the separate frit sections, which one or more coated surfaces abut the other frit section or sections. The configuration of an inlet split frit assembly may be the substantially the same as the outlet split frit assembly described herein.

In embodiments utilising the segmented inlet, preferably the column has an inlet flow distributor at its inlet end, e.g. to produce a curtain flow regime around a central flow. The inlet flow distributor is preferably similar or the same in configuration and structure to the outlet flow distributor described above.

Herein the term column means any tubular structure for performing chromatography on a sample. Accordingly, the column may be a straight column or a coiled column, preferably a straight column. Preferably, the column is a column that can be packed with a suitable media.

The column may be, for example, a large scale column used for industrial scale preparative chromatography, or a small scale column for preparative chromatography on small amounts of samples and/or in a laboratory environment.

Typically the column is a column for liquid chromatography but may, for example, be a column for supercritical fluid (SCF) chromatography. The flow paths for the SCF throughout the apparatus are appropriately pressurized in that case.

The column may be a column for analytical chromatography. The column may be, for example, a column for high performance liquid chromatography (HPLC), ultra-high performance liquid chromatography (UHPLC), flash column chromatography, fast protein liquid chromatography (FPLC) and other forms of chromatography. The column may comprise a capillary (as used in capillary chromatography).

Advantageously, the column in certain embodiments may be a standard, i.e. conventional, HPLC column, thereby allowing the invention to be employed by users on standard columns wherein only modifications at the column outlet and optionally the column inlet need be made, e.g. use of a modified frit assembly and/or flow distributor as herein described, together with the connection(s) to the reactant source(s) and processing unit(s).

The column may be an analytical column of an aforementioned type wherein the eluate/mobile phase reaction comprises a derivatisation to enhance detection or analysis of the components, and/or the eluate/mobile phase reaction comprises a protein modification. The eluate/mobile phase reaction may comprise, for example, a protein digestion, preferably for analytical purposes. The eluate/mobile phase reaction may comprise, for example, a catalytic reaction. The samples reacted in the eluate/mobile phase reaction may comprise, for example, biomolecules, food additives or ingredients, or pharmaceuticals. The products of the reaction may be fed directly into a stage of processing, such as mass spectrometry (MS), or to one or more further stages of chromatography, e.g. a second dimension chromatography and/or to one or more further stages of reaction.

Suitable columns, as is known, may be made of a wide variety of materials including, for example, metal (preferably stainless steel), glass, ceramic, polymer etc. The column may be made as a microfabricated or integrated fluidic chip structure (integrated chip columns). The column may be any suitable length; preferably columns are of length in the range 5 mm to 1000 mm (possibly longer), e.g. 50 to 200 mm, e.g. about 100 mm, especially for analytical, e.g. HPLC, applications. The column may be of any suitable diameter; preferably the column internal diameter lies between 300 μm and 1000 mm, e.g. standard internal diameters such as 4.6 mm diameter for HPLC. The column is preferably of circular cross section (i.e. transverse cross-section), although other shaped cross section columns may be used.

The chromatography which the invention is useful for, in different embodiments, may be analytical chromatography, e.g. high performance liquid chromatography (HPLC), ultra-high performance liquid chromatography (UHPLC), multi-dimensional or two dimensional high performance liquid chromatography (MDHPLC or 2DHPLC), flash column chromatography, fast protein liquid chromatography (FPLC), parallel detection chromatography, SCF chromatography and other chromatography, especially HPLC. The invention may be used in analyses involving protein or enzyme digestions or amino acids. It may be used in biodetection in natural products.

The chromatography which the invention is useful for, in embodiments, may be preparative chromatography, e.g. preparative-high performance liquid chromatography (PH-PLC), process chromatography, protein purification, enzyme purification, antibody purifications, small molecule purifications or synthesis, pharmaceutical purifications or synthesis, or natural product purifications or synthesis. The invention may further be utilized in chemical synthesis, for example nanoscale synthesis, low volume organic synthesis, organic or chiral selective synthesis.

The liquid chromatography which the invention is useful for, in embodiments, may be both analytical and preparative chromatography, e.g. where the eluate is both detected for analytical purposes and collected in purified fractions. The desired and collected product may be the reacted product. In other embodiments, the reacted product may be utilised for enhanced processing (e.g. detection) but a separate, unreacted stream of eluate is collected, e.g. for subsequent preparative use.

With regard to the type of mobile phase and stationary phase to be used, any suitable type of mobile phase and stationary phase, e.g. any suitable and/or known phases, may be used which are appropriate for the type of chromatography being performed, e.g. any known HPLC mobile phase and stationary phase when performing HPLC. With regard to the type of separation method that may be used, any suitable conventional methods may be used, for example, either isocratic or gradient elution, or displacement elution, either normal phase or reverse phase or hydrophilic or ion exchange or ion exclusion or affinity or chiral or size exclusion LC etc.

Where the chromatography is supercritical fluid chromatography, the mobile phase may be a conventional SCF such as carbon dioxide but is not limited thereto.

Apparatus utilizing the present invention and methods of the present invention may be used for a wide variety of applications, including, for example, purity analysis, component analysis, quality analysis, quantitative analysis, and isolation or purification on the analytical scale, the pilot scale or industrial scale. The reaction chromatography provided by the present invention may also be used in synthetic applications, e.g. pharmaceuticals, foods. Market applications include, for example, drug discovery, clinical analysis, environmental analysis, and diagnostic marker research in the fields of natural products, proteins, glycoprotein, phosphoprotein, metabolites and nucleic acids, for example. The invention is thus applicable, for example, in the pharmaceutical, chemical, biotechnology, biopharmaceutical, food and manufacturing industries.

The invention is applicable to packed columns. Packed column herein means a column containing any suitable bed for the stationary phase. Any conventional bed media may be packed inside the column as the column bed, depending on the type of chromatography being performed. The bed media may comprise, for example, particles or porous monolithic material (e.g. polymeric or ceramic monolithic bed), preferably particles. The bed media alternatively may comprise a membrane bed or any other bed. Particle sizes of the preferred particulate media may range, for example, between 1 μm and 150 μm, but no lower or upper limits on particle size limit the invention. A wide range of pore diameters may be used with porous media utilized in the invention depending on the type of chromatography; preferably pore sizes range between 30 Å and 3000 Å (3 and 300 nm). Porosities of a wide range may be used; preferably porosities lie in the range from 0% to 80%. Packing media may include various chemistries depending on the type of chromatography, for example alkyl bonded phases, typical polar bonded phases and chiral stationary phases. Integrated chip columns may use particles or porous monolithic beds.

The type of detectors which may be used in the processing means may comprise any conventional detector for column chromatography, e.g. ultraviolet or visible (UV/Vis), mass spectrometric (MS), fluorescence (FL), chemiluminescence (CL), refractive index (RI), conductivity (CD), evaporative light scattering (ELSD), decolorisation detectors etc. Moreover, any non-conventional detector for column chromatography may be used in the processing means, e.g. nuclear magnetic resonance (NMR) or infrared (IR) or antioxidant detectors, or any other bio-type detector. In some cases, in-column detection may be used, wherein a detector is positioned in the column bed so that, for example, the detector detects only the mobile phase from a particular radial region, especially the central region. Such detectors may comprise conductivity detectors.

In some embodiments, a single flow of eluate is reacted and processed as one flow stream. In other embodiments, preferably, a first portion of the flow of eluate is directed to a first processing unit or units and a second portion of the flow of eluate is directed to a second processing unit or units. The portions in such cases are processed separately from each other, i.e. the first and second processing units are separate. One portion of eluate may be reacted and the other not reacted. In this way, for example, a first portion comprising reacted eluate can be separately processed (e.g. detected) from a second portion that has not been reacted. Since the portions each comprise preferably eluate from a restricted radial region of the column (e.g. reacted eluate from a peripheral radial region and unreacted eluate from a central region), each portion should exhibit better resolved peaks or components than a conventional arrangement, which detects eluate gathered from across the whole width of the column via a single central outlet port, or otherwise collectively processes eluate gathered from across the whole width of the column. The invention can thereby provide, e.g., a chromatogram from the first portion and/or a chromatogram from the second portion, each with a higher resolution of peaks than if the portions were detected together. The efficient reaction provided by the invention further enhances such detection.

Preferably, the second processing unit(s) is/are a different type of processing unit(s) to the first processing unit(s). However, in some embodiments, it will be appreciated the first and second processing unit(s) may be the same type of processing unit(s) (e.g. they may each comprise the same type of detector), one unit processing a first portion and the other unit processing the second portion, as long as the portions are processed separately. However, preferably, the second processing unit(s) is/are a different type to the first processing unit(s) since the portions typically have different degrees of separation and/or different compositions (e.g. since one portion may be reacted and the other not) and it will be desirable to process them in different ways. As examples, the first and second processing units (and optionally further processing unit(s) where the eluate is separated into third or further portions) may each independently comprise one or more of: a detector, a waste reservoir, a fraction receiver or collector, and a chromatography column inlet. Thus, the processing for each portion is preferably (independently) one or more of: detecting, collecting fractions, sending to waste, and sending to a chromatography column inlet.

Preferably, in some embodiments, the processing of one eluate portion, e.g. the first portion, comprises detecting the portion separately from the other portion(s), e.g. for analytical chromatography. Preferably, in some embodiments, the processing of one portion, e.g. the first portion, comprises collecting fractions from the portion separately from the other portion(s), e.g. for preparative chromatography or for multidimensional HPLC, either in a comprehensive analysis, or in a heart cutting analysis. Preferably, in some embodiments, the processing of one portion, e.g. the second portion, comprises sending the portion to a column inlet separately from the other portion(s). In some embodiments, portions may be sent to multiple separate columns for the purpose of providing different selectivity in separation and analysis. Preferably, in some embodiments, the processing of one portion, e.g. the second portion, comprises sending the portion to waste separately from the other portion(s).

Preferably, a first portion (e.g. typically a portion having a relatively higher resolution of separation) is separately detected and/or collected from a second portion (e.g. typically a portion having a relatively lower resolution of separation). More preferably, the first portion in such embodiments is a portion emanating from a central radial region of the column.

In some embodiments, it may be desirable to detect both a portion emanating from the central radial region, and also a portion from the outer radial region as both regions may exhibit better resolved peaks than a conventional arrangement with a single central outlet port, i.e. both streams of eluate may be utilised for analytical and/or preparative purposes when segmenting the flow. Without being in any way limiting on the scope of the invention, this is believed to be due to the fact that a portion of eluate taken from a restricted radial region has a smaller axial spread of sample than eluate taken from across the full width of the column. One portion is preferably reacted with the reactant flow according to the invention, whilst the other is not. Thus different degrees of specificity in detection can be provided in each portion of eluate flow.

Preferably, the first processing means comprises a first detector. As an example, the first processing unit may comprise a detector, for detecting a sample present in the eluate, and the second processing unit may comprise a detector of the same or different type to the first, typically which is reached without passing the detector of the first processing unit. As another example, the first processing unit may comprise a detector as described before and the second processing unit may comprise the inlet of the same or another chromatography column so that the second portion is subjected to at least a further round of chromatography, e.g. involving recycling of the mobile phase. Preferably, in accordance with the invention, at least one of the portions is reacted eluate and the other is non-reacted eluate.

The second processing unit may comprise a valve which can be controlled by a control system and which is switchable between a first position that allows flow of the second portion to the inlet of the same or another chromatography column and a second position that allows flow of the second portion elsewhere, e.g. to a detector, a fraction collector, another column or waste.

As yet another example, the first processing unit may comprise a detector as before (a first detector) and the second processing unit may comprise a detector (a second detector), optionally where the second detector may provide a measurement that may be used (e.g. by the control system) to determine whether to flow the second portion to the inlet of the same or another chromatography column so that the second portion is subjected to at least a further round of chromatography. The control system is preferably provided which preferably receives the signals from the one or more detectors comprised in the first and/or second processing means. The control system may, for one or more of the processing means, control the operation of one or more valves, based on a signal from a detector in the processing unit, so as to direct a portion of eluate after it has passed the detector to a desired destination, e.g. to waste or a column inlet. Thus, the apparatus may execute a form of data-dependent processing.

Where a processing means comprises the inlet of a chromatography column, the processing means may further comprise a vessel or flow loop in which eluate to be further chromatographed is gathered and preferably re-concentrated before the further chromatography.

In these various ways, for example, the invention provides a column with an outlet configured to selectively direct a portion of the eluate flow to a first processing unit, e.g. a detector, while it directs another portion to another processing unit different to the first processing unit. Preferably, for analytical purposes, the first processing unit comprises a detector arranged so that the first portion is detected separately from the second portion. Preferably, for preparative purposes, the first processing means comprises a fraction receiver arranged so that fractions of the first portion are received separately from the second portion (where the first processing unit comprises a fraction receiver, it may also comprise a detector).

It will be appreciated that many other processing means, and combinations thereof, could be employed and some of these are discussed in more detail herein below. Herein, the processing unit includes the route taken by a portion of eluate after it leaves the column, so that the eluate portions may, for example, in certain embodiments be directed to the same detector but by different routes so that the portions are detected (processed) separately, e.g. not at the same time in that case. In most cases, it is preferred, however, that the separate portions follow completely separate routes after being split at the column outlet.

In some embodiments, the different portions of eluate split at the outlet could be recombined downstream of the outlet. The portions may be recombined after the portions have undergone separate processing. For example, the portions may be recombined after one portion, preferably the central portion, has been detected separately from the other portion (s). The recombined portions, for example, may then be subjected to one or more further chromatographic separations, optionally after re-concentration of the portions.

A plurality of apparatus according to the invention may be linked together, that is one (or more) of the portions of eluate at the outlet of the column may be fed into the inlet of a further column, i.e. of a further apparatus according to the invention. Thus, a cascade of columns in accordance with the present invention may be linked together. Alternatively, the further column may be a conventional column or another column which is not a column in accordance with the present invention. In general therefore, the invention may comprise directing the flow of one (or more) of the portions of eluate to a further column for further chromatographic separation. In this way, a portion (or more than one portion) of eluate in which components of a sample have not been adequately separated, i.e. resolved, may be fed into a further column and subjected to chromatography therein in order to further separate the components, or alternatively, reaction products may be separated on the second or subsequent columns. The number of columns which may be connected in this cascading way is not particularly limited. For example, two, three, four, or more columns may be connected together in such series. The eluate may be re-concentrated before injection into each further column or columns. The portion of eluate that is directed to further chromatographic separation is preferably the portion that emanates from the outer or peripheral radial region of the column, as components therein are typically less well separated than they are in the portion that emanates from the central region, but the portion of eluate that emanates from the central portion could optionally be directed for further chromatographic separation, as would be the case in multidimensional or two dimensional HPLC.

As a further variation on the foregoing embodiments, the eluate may be recycled, e.g. via conduits, i.e. directed back to the inlet of the same column for one or more further passes through the same column (i.e. one or more rounds of chromatography). In particular, the eluate or one (or more) of the portions of eluate separated at the outlet of the column may be fed back into the inlet of the column. In this way, a portion (or more than one portion) of eluate in which components of a sample have not been adequately separated, i.e. resolved, may be fed into the column again and subjected to further chromatography therein in order to further separate the components. The eluate is preferably concentrated before re-injection back into the column for the one or more further passes thorough the column.

The invention may comprise further known components of a chromatography apparatus in various embodiments. For example, the invention may further comprise at least one mobile phase reservoir to supply mobile phase to the inlet of the column. The invention may further comprise at least one pump to pump the mobile phase from the at least one mobile phase reservoir through the column. In some embodiments, for example in which two or more separate portions of mobile phase are introduced through a multiport inlet, two or more pumps may be used (e.g. one for each portion). However, it may be possible to use a single pump even for the cases of multiple mobile phase portions being introduced at the inlet by using flow regulation, such as an arrangement having a single pump but with pressure restrictions in the lines which carry the mobile phase to vary the degree of flow restriction independently in each line. The invention may further comprise at least one pump to pump reactant from the reactant source or reservoir into the column outlet. In some embodiments, for example in which two or more reactants are introduced, two or more pumps may be used (e.g. one for each reactant source). The invention may further comprise at least one sample injector, e.g. an injection valve, to inject a sample into the mobile phase upstream of the column inlet. The invention may further comprise one or more pressure regulators or flow restrictors to balance the flow from the numerous exit ports at desired levels, the one or more pressure regulators preferably being located downstream of the column outlet. The apparatus is preferably under the control of a Control and Data Collection System, which e.g. comprises a computer and control electronics. The Control and Data Collection System preferably is for controlling (in each case where the component is present) the pumps for pumping of mobile phase and reactant, the sample injector for sample injection and/or the one or more pressure regulators to balance the flow through the exit ports. The Control and Data Collection System preferably is for receiving, and optionally processing, data from one or more detectors of the processing unit(s). The Control and Data Collection System may also provide an output of the data, e.g. with or without processing thereof, as required. The Control and Data Collection System may additionally control other components of the apparatus.

BRIEF DESCRIPTION OF THE DRAWINGS

FIG. 5A shows a perspective view of a preferred embodiment of a frit assembly for use with the invention; FIG. 5B shows the underside view of the embodiment looking in direction of arrow A; and FIG. 5C shows a side cross section view of the embodiment taken on line B-B.

FIG. 5D shows a perspective view of another preferred embodiment of a frit assembly for use with the invention; and FIG. 5E shows the underside view of the embodiment.

FIGS. 5F and 5G schematically show respective further embodiments of frit assemblies for use with the invention.

FIGS. 5H and 5I schematically show embodiments of exit capillary arrangements at the column outlet for use with the invention.

DETAILED DESCRIPTION OF EMBODIMENTS

In order to further understand the invention, but without limiting the scope thereof, various exemplary embodiments and experiments are now described with reference to the accompanying drawings.

Figure 1:
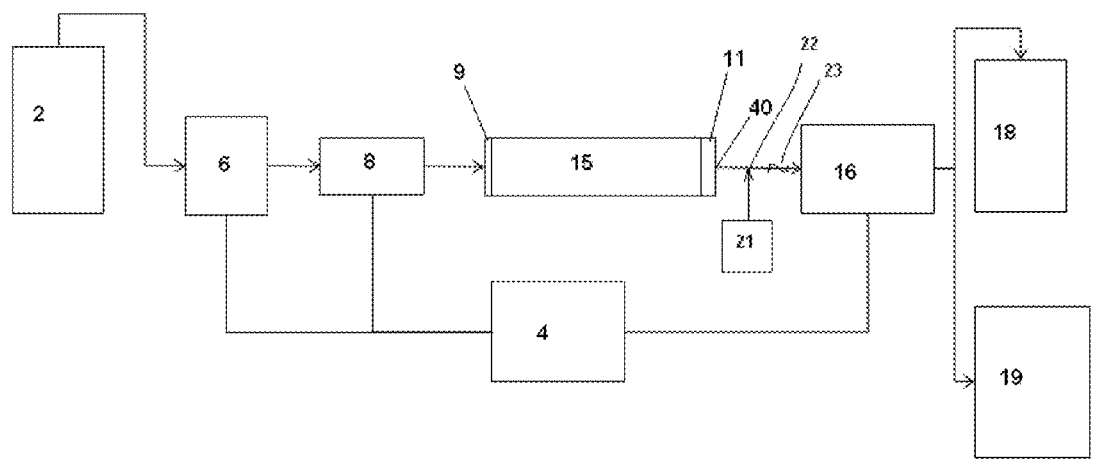
FIG. 1 shows schematically in flow-chart form a conventional configuration of an HPLC system.

In a conventional configuration of an HPLC system (as shown schematically in FIG. 1 in the form of a flow chart), one or more bottles of mobile phase solvent(s) 2 are delivered via tubing to a solvent delivery system 6 that employs a pump pumping at high or low pressures, or are delivered via tubing by force of gravity (low pressure only). The solvent delivery system 6 delivers desired mobile phase solvent or mixtures thereof (herein simply termed solvent) through a sample-injection port or valve 8 where a sample is introduced into the solvent flow and then into a chromatographic column 15 packed with a stationary phase or bed or provided with a monolithic stationary phase. The column is typically a circular cross section cylindrical column. The flow through the column 15 is radially dispersed over the full width of the cross-section of the column bed by a head or inlet frit 9 as well as by the column bed itself and subsequent chromatographic separation then occurs as the sample is carried by the mobile phase solvent down the length of the column. At the exit or outlet of a conventional HPLC column, the out flowing mobile phase or eluate is gathered by a second or outlet frit 11 typically held in place by an end fitting fitted to the outlet end of the column so that the entire cross section of the flow is delivered to a small exit port 40 located at the centre of the cross section of the column. That is, material from outer radial regions of the column near the wall is forced radially inwards to pass, together with material that has passed through the central radial region of the column, through the single central exit port 40. Separated components of sample are then carried by the eluate flow stream through suitable connective tubing into a detector 16, which generates a chromatographic trace.

In analytical chromatography, the separated components may be either sent to waste 18 after detection, or destroyed as part of the detection. In preparative chromatography, a portion of the eluate flow is detected and that is used as the basis for collecting desired components from the flow stream using a reservoir or fraction collection device 19. The system is under the control of a Control and Data Collection System 4, e.g. a computer and associated control electronics, which in particular controls the solvent delivery system 6 and injector 8 and controls and receives data from the detector 16, as well as controlling other components. The Control and Data Collection System 4 may also process the data for output, e.g. as a chromatogram.

In many instances, it is necessary to perform a post-column reaction on the eluate stream, for example to allow analysis by fluorescence, chemiluminescence, or decolorisation reaction. In such cases, a separate reactant source unit 21 downstream of the column outlet is employed to supply a reactant (reagent) into the eluate at a zero dead volume t-piece 22. The reacted sample components are then detected in the detector. This additional step, as well as the plumbing and equipment for the post column reaction, increases the time, labour and cost of detection. Typically a reaction coil 23 is employed to enhance the reaction. Broadening of the component peaks, i.e. loss of resolution may also occur as a result of the post column reaction.

Figure 2:
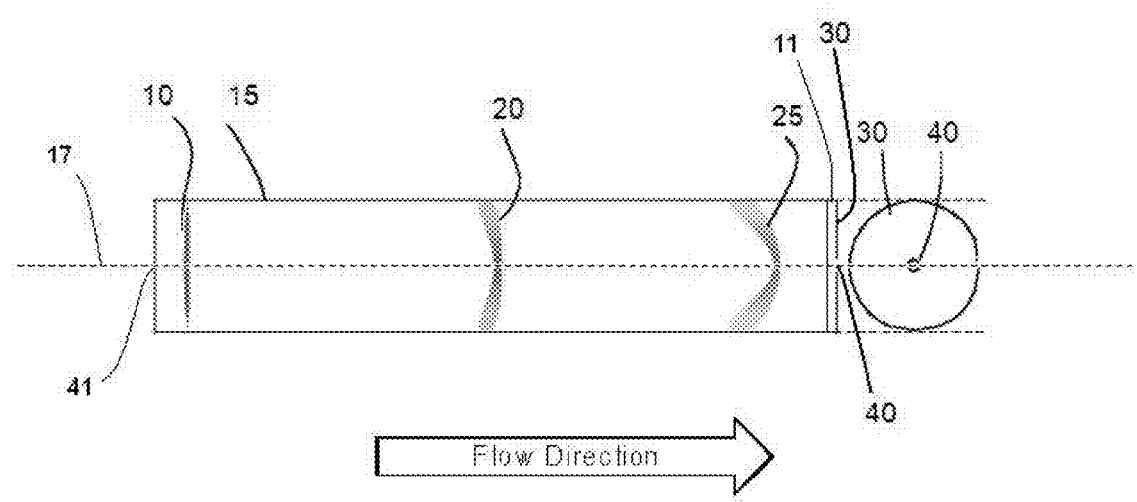
FIG. 2 shows schematically an axial cross-section side view through a conventional packed chromatography column with a single sample component eluting.

As illustrated in FIG. 2, which schematically shows an axial or longitudinal cross-section side view through a conventional packed chromatography column 15, a sample component applied to the head of the column from the injector via a single centre inlet port 41 accumulates there in the shape of a relatively thin, flat band 10. In three dimensions, the band 10 resembles a thin, flat disc that is bounded by the inner diameter of the column casing or wall. During separation on the column, and as the band 10 of sample is carried down the column by the mobile phase, the band begins to change shape as shown by the band at 20 and as described in more detail in the introduction above. Briefly, the centre of the band located on and around the central or longitudinal axis 17 of the column, moves faster than the perimeter of the band nearer the wall, drawing the band of material into a sort of bowl or cup shape as shown clearly by the band at 25. Furthermore, the sample near the column wall begins to spread out (broaden) and become more dilute.

This phenomenon is progressive, such that it is most pronounced as the fluid leaves the column at the exit end or outlet of the column. At the end of the column 30, the "bowl" of material, begins to exit the centre exit hole or port 40 located on the central axis 17 after passing through a thin frit layer 11 with minimal impedance of lateral flow. To the right hand side in FIG. 2 is shown the end-on view of the end 30 of the column with the centre port 40 in the middle. The goal of the conventional arrangement is to gather the full cross section of the sample "band" to the centre port 40, and direct it to the detector in as sharp a peak as possible.

Figure 3:
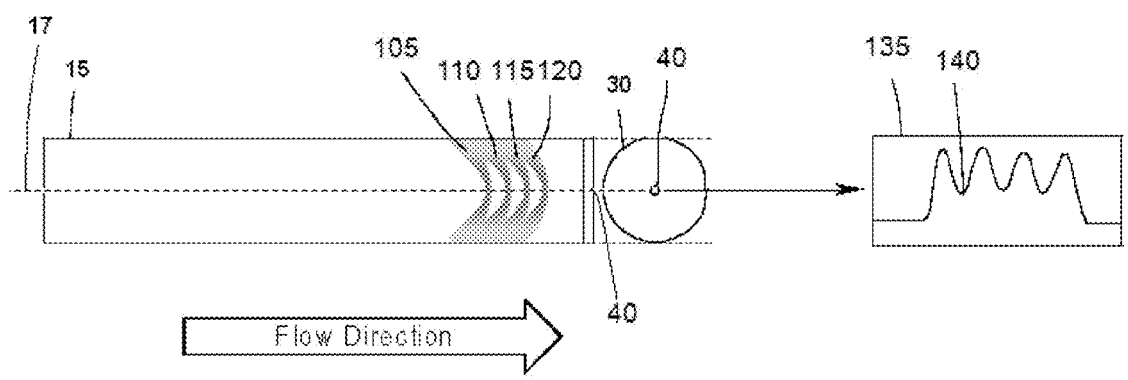
FIG. 3 shows the view of FIG. 2 with four different sample components eluting.

When multiple components are applied to a packed column, their different chemical affinities for mobile and stationary phases in the column cause them to move at different rates through the column than each other. That is the basis of separation in an LC column. FIG. 3, which is analogous to FIG. 2 shows four different sample components 105, 110, 115, 120 that have been partially resolved (i.e. separated) from one another over the length of the column 15. It should be appreciated in the schematic example shown in FIG. 2B that, in the centre of the column, i.e. on the central axis 17, peaks are completely resolved. As this set of components 105, 110, 115, 120 exits the single central hole or port 40 at the centre of the chromatography column outlet, with liquid from across the full width being forced through the port, the peaks in the resulting chromatogram 135 display partial or incomplete resolution. That is, there are distinguishable peaks but they are not completely separated from each other at the early and late part of each peak, e.g. in the inter-peak region 140.

In contrast to the conventional arrangement described, in preferred embodiments of the present invention, the outlet of the column is configured with a plurality of exit fluid ports in contrast to the single exit port 40 of the conventional arrangement. As described in more detail hereinafter, preferred embodiments may use an end or exit fitting (also termed end cap) on the outlet end of the column that has been modified to be unlike a conventional LC end fitting. A preferred modification is that the outlet frit and/or end fitting are designed to drain the mobile phase (eluate) from the column through multiple ports that are positioned at different points in the transverse (radial) cross section of the column when the frit and/or fitting are positioned at the outlet. In this way, the mobile phase being drained through the multiple ports emanates from different regions of the column, more particularly different radial regions of the column. This allows segregation of the different fluidic components across the diameter of the column. The flow from the multiple ports can be treated as separate portions and processed differently. By restricting the portions of eluate to limited radial regions of the column, each portion may show improvements in separation efficiency compared to the conventional case where eluate from across the whole column is gathered together and detected as one stream. In some embodiments, however, eluate from across the whole column may be reacted (and processed) as one.

Various exemplary embodiments of the invention are now described.

A first preferred feature of the invention is that the frit at the outlet is modified to separate and segregate mobile phase arriving from the centre of the column cross section from mobile phase arriving from the region surrounding the centre (i.e. from the perimeter region). Thus, the flow of eluate is split by the frit into a portion which has travelled through the centre of the column and a portion which has travelled through the perimeter region. A second preferred feature is that the centre and perimeter flows are then taken off into different exit ports in a flow distributor (e.g. steel end fitting or cap) that is typically fitted (e.g. screwed) to the end of the column. It is possible in some embodiments to use such a distributor without the split-frit which splits the eluate since the flow distributor with multiple ports may alone perform splitting of the eluate flow into the different portions, e.g. where the surface of the flow distributor which faces the frit lies close to the surface of the frit, preferably contacting the surface of the frit.

Figure 4:
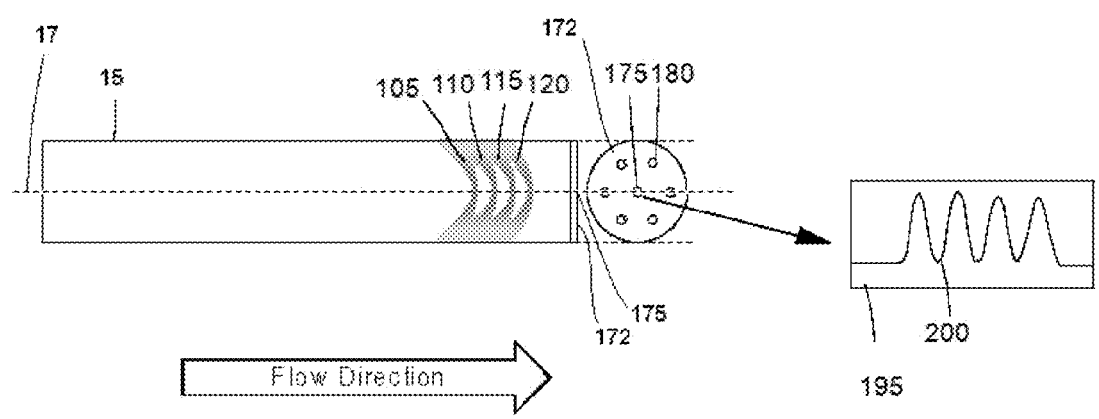
FIG. 4 shows schematically an axial cross-section side view through a packed chromatography column in accordance with the invention showing the principle of a flow distributor at the outlet to enable reaction chromatography.

FIG. 4 illustrates schematically the principle of a flow distributor at the outlet of the column 15, which is a packed column, e.g. for HPLC. FIG. 4 shows a schematic longitudinal cross sectional side view of the column similar to FIGS. 2 and 3. To the right hand side of the longitudinal cross section side view is shown an end-on view of the column outlet (i.e. an end-on view of the flow distributor 172 on the end of the column). The flow distributor comprises a centre outlet port 175, positioned similarly to the single centre port 40 of the conventional arrangement that can receive and transmit eluate flowing from the central radial region of the cross section of the column (i.e. a region located on the central axis 17 of the column). The flow distributor further comprises six peripheral ports 180 located equally and symmetrically spaced around the central port 175 that can receive and transmit eluate that is flowing in the perimeter region. Any of the peripheral ports, e.g. half of them (in this case three), could be used as reactant ports. That is, reactant may be flowed from a reactant source (not shown) through one or more of the peripheral ports into the column outlet to encounter the eluate flowing in the peripheral region and react therewith. This reaction chromatography is described in more detail below.

The right hand side of FIG. 4 illustrates the better resolved peaks in a resultant chromatogram (trace 195 showing baseline resolution of the peaks, 200) which arises from detection of only the eluate from the central port 175. The chromatogram 195 shows an improvement in resolving power compared to the chromatogram 135 obtained using the conventional column arrangement as shown in FIG. 3 where all the eluate from across the full cross section of the column is gathered together and detected. The eluate from the one or more peripheral ports 180 collectively forms one portion of eluate that is not processed with the eluate from the central port 175. For example, in one embodiment in which eluate from the central port 175 is detected using a detector, the eluate from the peripheral ports 180 may instead be reacted, as hereafter described in more detail, and detected using another, separate detector and/or separately collected and/or sent to the inlet of the same or another column for a further chromatographic separation in order to better resolve the components, optionally after being reconcentrated before such further chromatographic separation. The peripheral eluate also exhibits better resolved peaks than in a conventional arrangement as shown in FIG. 3. Without being in any way limiting on the scope of the invention, this is believed to be due to the fact that a portion of eluate taken from a restricted radial region has a smaller axial spread of sample than eluate taken from across the full width of the column.

There are different possible ways to design an outlet frit 11 suitable for the purpose of segregating flows of mobile phase from the outlet of the column. FIG. 5A shows a perspective view of one preferred embodiment of a frit assembly 220, with FIG. 5B showing an underside view of the embodiment looking in direction of arrow A and FIG. 5C showing a side cross section view taken on line B-B. In the embodiment shown, the frit assembly is assembled from sections of frit, i.e. a central, circular frit disc 235 and surrounding annular concentric frit ring 245 both made of porous material conventionally used as frit material, e.g. steel, which are separated from each other by a solid, non-porous flow barrier in the form of concentric ring 240, e.g. made of polymer such as PEEK. The non-porous intervening ring 240 prevents lateral flow of eluate between the two frit sections 235 and 245, thus keeping the central and peripheral eluate flows separate. The width of the non-porous ring 240 is lower than the width of the frit sections in this case, thereby to reduce drag on separated components in the eluate flow. The disc and rings 235, 240, 245 are fixed together and held inside a ring shaped, profiled outer fitting 250 also made of solid, non-porous material, e.g. PEEK, which acts as a fitting to the end of the column as described below.

The aforesaid parts 235, 240, 245, 250 are thus assembled so that they fit together to form the assembly 220 which acts as a frit cap, wherein the outer ring 250 is dimensioned and profiled with an extended peripheral edge 224 which fits over the end of the column so that the under-side 222 of the frit cap is push-fitted (i.e. friction fitted) over the end of the column. Frit assemblies for use with the invention, like the assembly 220, typically may be push-fitted as shown or screwed onto the column end, but are preferably applied by push or friction fit. The over-side of the frit cap 225 in use is in contact with the steel end fitting (described in more detail hereafter) once the end fitting is screwed onto the end of the column. The non-porous intervening ring 240 protrudes slightly above the face or edge of the frit sections 235 and 245 on the downstream side, as evident in the protruding edge 241 of the non-porous ring 240 shown in the side view of FIG. 5C. The protruding edge 241 of the non-porous ring 240 can seal against the flow distributor, i.e. the underside of the flow distributor, to thereby separate zones of eluate adjacent each frit section. In this embodiment, the peripheral zone of eluate (adjacent outer frit section 245) is thus separated from central zone of eluate (adjacent central frit section 235). In a similar way, the non-porous, outer fitting or ring 250 also protrudes slightly above the face or edge of the frit sections 235 and 245 on the downstream side, which enables it to seal the against the flow distributor as well (to form an outer seal).

FIGS. 5D and 5E show views of a similar frit assembly construction to that shown in FIGS. 5A, B and C except that the frit disc 235' and rings 240' and 245' are of different relative areas thereby splitting the eluate flow into portions from central and peripheral regions of different relative transverse area. As examples, the ratio of the area of the outer frit section 245 (245') to the area of the central frit disc 235 (235') may vary, e.g. from 90%:10% to 50%:50% but typically from 80%:20% to 50%:50% with ratios outside this range also possible. As examples the aforesaid ratio may be about 70%:30% or 75%:25%. Preferably, the said ratio is about 2:1. The ratio of the areas of the frit sections may be a means to vary the ratio of the respective volumes of the split portions of eluate flow. In some embodiments, it may be possible to use a central frit disc 235 (235') that has a different, e.g. lower, density compared to the frit sections 245 (245').

FIGS. 5F and 5G show further frit designs which could be used in the present invention to split the eluate flow at the column outlet, in which a central porous frit disc 535 is surrounded by a plurality of porous frit discs 550, each of the frit discs 535 and 550 being located in a non-porous body 540, which thereby prevents lateral flow of eluate between the two frit sections 535 and 550. Other arrangements similar to those in FIGS. 5F and 5G could have more or less than the six peripheral frit discs 550 shown. The relative areas of the central and peripheral frit discs 535 and 550 may be varied, with examples of different relative areas being shown in FIGS. 5F and 5G.

In certain other embodiments, as shown in FIGS. 5H and 5I, the column outlet 580 may be provided with a plurality of exit capillaries 585, 590 to channel the eluate flow in separate portions out of the end of the column, wherein a radially central capillary 585 is arranged to channel the first portion of the flow from the central region of the column and ten capillaries 590 peripherally arranged around the central capillary 585 are provided to direct the second portion of the flow. Thus, the first and second portions are channeled in separate capillaries and thus are split from each other. Preferably, in such embodiments, frits 592 are provided in the ends of the capillaries as shown in FIG. 5I. The total number of capillaries may be varied, e.g. 5, 6, 7, 8, 9, 10, 11, or 12 or more capillaries.

Figure 6A:
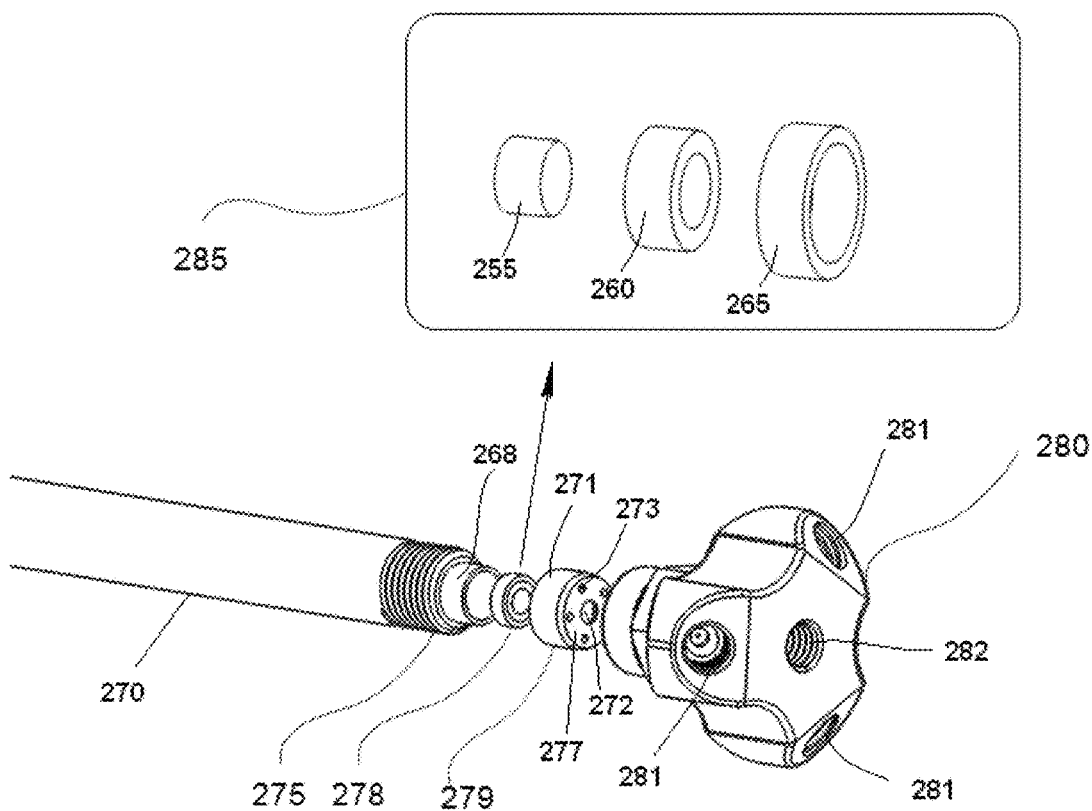
FIG. 6A shows, in exploded view, an embodiment of the invention having a split section frit and four port end fitting.

FIG. 6 shows, in exploded view, an embodiment of the invention, which could be used, for example, with a standard analytical HPLC steel column 270 of 4.6 mm internal diameter. The embodiment in FIG. 6A uses a split frit assembly, 278, 279, and a flow distributor in the form of a steel end fitting 280 having multiple flow channels therein with corresponding fluid ports 281, 282. The parts (inset 285) of the split section frit 278 (corresponding to parts 235, 240 and 245 in FIGS. 5A-E) are assembled and placed at the column outlet. The frit parts 285 comprise a central frit disc section 255 held in a non-porous intermediate PEEK ring 260, with ring 260 in turn held in an outer peripheral ring frit section 265. Over the frit parts 285, there is a fitting 279, i.e. an outer cap made of PEEK, which acts as a flow adapter and serves to align the respective separated flow paths through the split frit 278 with respective fluid ports 281, 282 of the end fitting 280 as described later. The fitting 279 comprises a main body 271 which closely fits over the end 268 of the column (by friction fit) and encloses the frit parts 285 of the split section frit 278 at the column end. In an alternative arrangement, instead of friction fit, the fitting 279 could fit to the end of the column by a screw connection (i.e. an internal thread inside the main body 271 of the fitting 279 could screw onto an external thread on the end 268 of the column).

The fitting 279 has a radially central aperture 272 which is aligned with the central frit section 255 of the split frit to thereby allow passage through the aperture 272 of eluate emanating from the central radial region of the column which has passed through the central frit section. The fitting 279 also has a plurality of, preferably equally spaced, peripheral apertures 273 (in this case 5 apertures) which are positioned peripherally around the central aperture 272 and lie in an annular recess in the end face 277 of the adapter. It will be appreciated that the apertures 273 could be circular or they could be slits or of some other shape. The peripheral apertures 273 in this case are radially aligned with the peripheral frit section 265 of the split frit. The apertures 273 thereby allow passage through of eluate emanating from the peripheral radial region of the column that has passed through the peripheral frit section 265. The peripheral eluate collected through apertures 273 in this way is communicated into the annular recess in which the apertures 273 lie in the end face 277 of the fitting 279.

The steel end-fitting or end-cap 280 is screwed, either hand tightened or tightened with the aid of a tool if necessary, onto the external screw thread 275 on the outside of the column end. The end-fitting 280 provides one or more fluid ports, in this case three fluid ports, 281, for fluid communication with mobile phase exiting the column from the peripheral radial regions of the column (i.e. via peripheral frit section 265 and peripheral apertures 273) and a central fluid port 282 for communication with mobile phase exiting the column from the central radial region of the column (i.e. via central frit section 255 and aperture 272).

When assembled, the underside of the tightened end fitting 280 (not visible in the figure) contacts the end face of fitting 279. The annular peripheral recess described in the end of fitting 279 containing apertures 273 is aligned with and in fluid communication with the peripheral ports 281 so that the peripheral flow of eluate through the peripheral apertures 273 is thereby in fluid communication with the peripheral ports 281 in the end fitting 280. The annular nature of the recess means that rotational alignment of the peripheral ports 281 with the peripheral apertures 273 is not required. Eluate in communication with peripheral ports 281 emanates from the same peripheral radial region and thus is preferably processed together as one portion of eluate, e.g. reacted and detected. Most typically, a reacted eluate flow from the peripheral ports 281 will be processed as one portion. However, it will be appreciated that flow from two or more peripheral ports could be processed separately. Indeed, the eluate flow from each peripheral port could be processed separately. One or more of the peripheral ports are preferably utilised as reactant ports. That is, reactant from a reactant source (not shown) is introduced into the column outlet through one or more of the peripheral fluid ports 281.

The central aperture 272 in the fitting 279 on the other hand is in fluid communication with the central port 282 of the end fitting. The eluate from central port 282 of the end fitting thus emanates from the central radial region of the column and is processed differently to the eluate from the peripheral ports. The eluate from central port 282 may flow unreacted to a separate detector for example. In another case, the central port could be closed or capped so that only peripheral ports 281 are used as reactant and product ports.

The fluid ports 281, 282 have internally threaded surfaces (female threads) to accept a screw fitting for plumbing to a reactant source, detector etc. as described below. Alternatively, it is possible to arrange the ports to have a male thread, e.g. male thread on a protruding portion, onto which is screwed a fitting for plumbing.

Figure 6B:
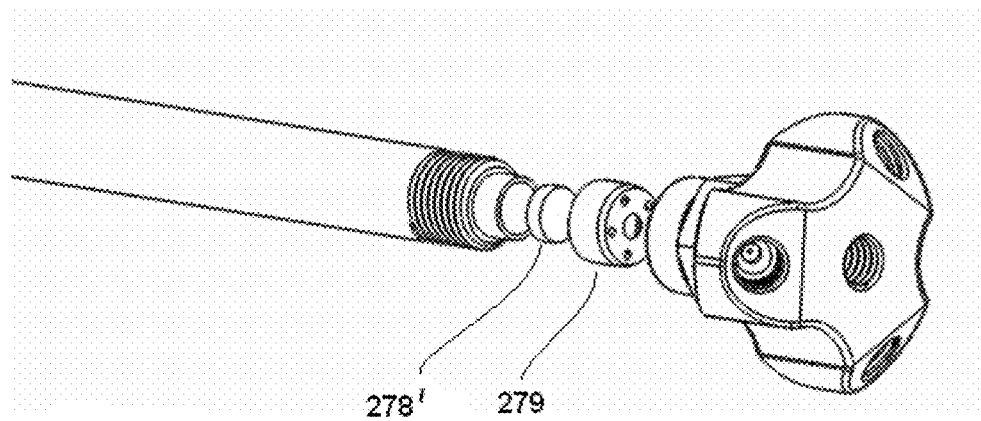
FIG. 6B shows a similar embodiment to FIG. 6A but having a single piece frit.

The embodiment in FIG. 6B is largely the same as shown in FIG. 6A but instead of the split section frit 278 it uses a frit assembly that has a single frit piece 278' inside the fitting 279, wherein the fitting 279 divides the flow at the downstream side of the frit piece by means of its apertures 272 and 273.

Figure 7:
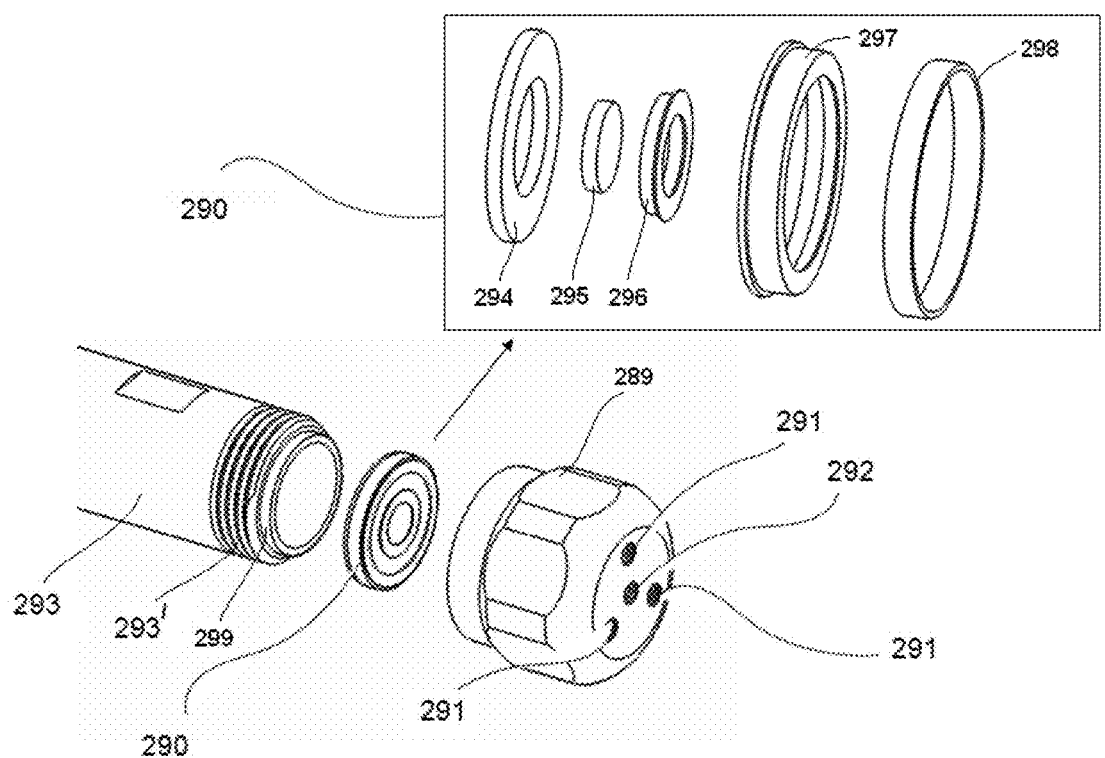
FIG. 7 shows, in exploded view, a further embodiment of the invention having a split section frit and four port end fitting.

FIG. 7 illustrates an exploded view of an example of a column 293, having at its outlet an externally threaded end portion 293', on which is screwed end fitting 289, which has an internal threaded surface for this connection. A split frit assembly 290, having frit parts as shown (see exploded view inset), is push-fitted over a portion 299 of the column end having a smaller external diameter than the threaded portion 293'. The split frit assembly 290 is held in placed once the end fitting 289 is screwed on the end of the column. The split frit assembly 290 in this embodiment comprises a central frit disc 295 and peripheral frit ring 294 which are separated from each other by non-porous PEEK ring 296 as a flow barrier. The split frit sections are held in outer PEEK ring fitting 297 which functions as a push fitting cap to fit over the end 299 of the column. The fitting 297 is further secured to the column end with annular steel band 298 which grips the circumference of the PEEK fitting 297.

In the FIG. 7 embodiment, the fitting 297 is different to the fitting 279 acting as flow adapter in FIG. 6. In this example, the underside of end fitting 289 seals against the non-porous parts (i.e. parts 296, 297) of the frit assembly 290 to thereby keep fluidly separate the portions of eluate flowing from the frit sections 295 and 294. The end fitting 289 has one central fluid port 292 at its centre and three peripheral fluid ports 291 surrounding it, although it should be understood that the present invention contemplates any number of peripheral ports 291, e.g. one or more peripheral ports 291. Preferred examples may have from 3 to 10 peripheral exit ports, particularly 3, 4, 5, 6, 7 or 8 peripheral ports. End fittings with 3 and 6 peripheral ports are good examples. Furthermore, the present invention contemplates any number of central fluid ports (i.e. those ports that communicate with a flow of eluate from a central radial region), e.g. one or more central ports. Preferably, however, there is one central port as in the embodiment shown. The end fitting central port 292 lies radially in the central region of the column and is radially aligned with the central frit section 295 and thereby communicates with the portion of eluate flow through the central frit section. The three peripheral ports 291 lie radially in the peripheral region of the column and are radially aligned with the peripheral frit ring 294 and thereby communicate with the portion of eluate flowing through the peripheral frit ring. The fluid ports 291, 292 have internally threaded surfaces to accept a screw fitting for plumbing as described below.

Figure 8A:
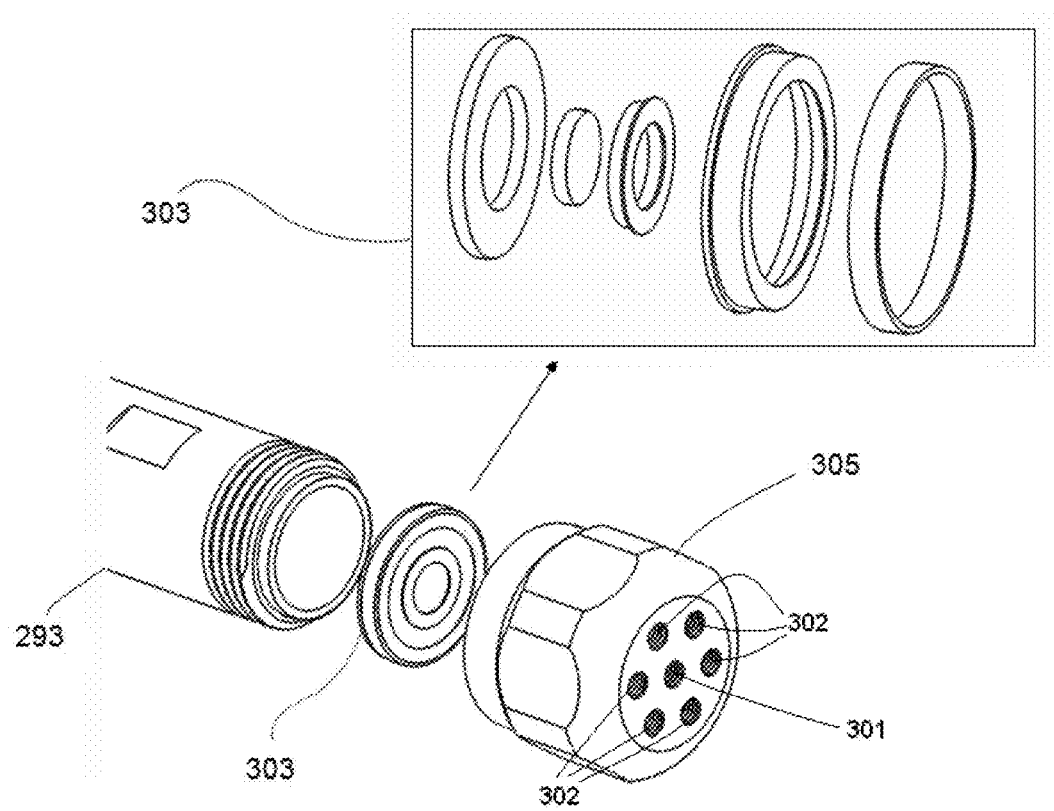
FIG. 8A shows, in exploded view, a still further embodiment of the invention having a split section frit and seven port end fitting.
Figure 8B:
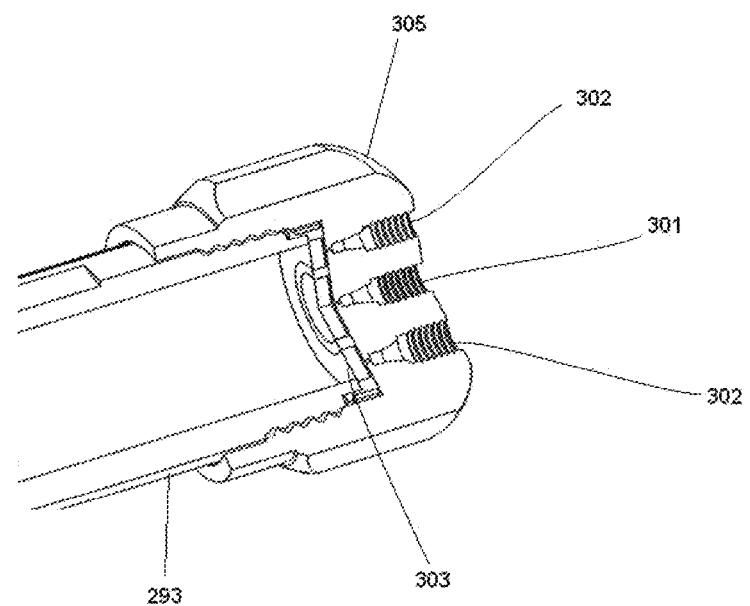
FIG. 8B shows the assembled embodiment of FIG. 8A in a cut-away view.

FIG. 8A illustrates an exploded view of an alternative frit assembly 303 and end-fitting 305 generally similar to that shown in FIG. 7. In this example though, the end-fitting 305 has six peripheral fluid ports 302 around one central port 301. The assembled frit assembly 303 and end-fitting 305 are shown in FIG. 8B, which has been cut away to show the relationship of the assembled parts inside.

Figure 9:
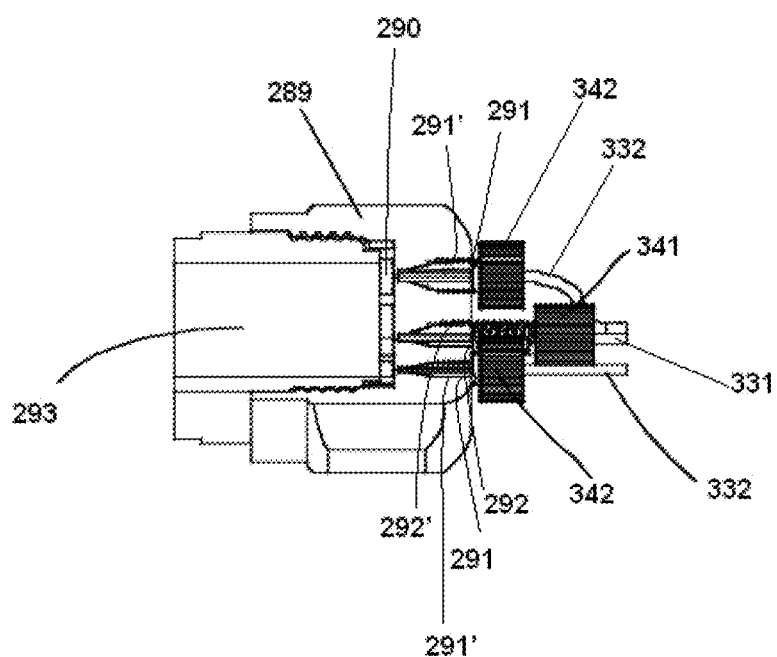
FIG. 9 shows a cut-away side view of the embodiment shown in FIG. 7, shown in assembled form and with exit plumbing attached.

FIG. 9 illustrates a cut-away side view of the same four-port end fitting shown in FIG. 7, but shown assembled on the column 293 together with fluid plumbing attached. It can be seen more clearly from this view that the fluid ports 291 and 292 comprise respective channels 291' and 292' running through the end fitting 289 from its inner surface which is in fluid communication with the frit assembly 290 to its outer surface.

In one embodiment, an exit plumbing tube 331, of standard type for HPLC, is fitted to the centre fluid port 292 by means of male screw fitting 341. Plumbing tubes 332, again of standard type, are fitted to the peripheral ports 291 by screw fittings 342 of the same type as screw fitting 341. The screw fittings 341 and 342 are screwed into the channels 292' and 291' of the ports 292 and 291 respectively, which channels carry an internal (female) screw thread for this purpose, and the plumbing tubes 331, 332 are thereby compression fitted. It will be appreciated that in other designs the plumbing could be fitted to the ports by means of a female screw fitting which fits to a male port on the end fitting.

The end fitting 289 is tightly screw fitted on the end of the column 310 so that inner surface or underside of the end fitting 289 contacts the end face of the frit assembly 290 and thereby the respective central and peripheral portions of eluate passing through the frit are in separate fluid communication with the respective central and peripheral ports 292 and 291 of the end fitting. The underside of end fitting 289 seals against the non-porous parts (i.e. parts 296, 297) of the frit assembly 290 to thereby keep fluidly separate the portions of eluate flowing from the frit sections 295 and 294 into the respective ports 292 and 291.

It will be appreciated that many further embodiments of the present invention may be devised to provide a segmented flow at the column outlet.

It can be seen from the foregoing description that the present invention has the great advantage that it can be practiced using existing conventional packed chromatography columns. By segmenting the eluate flow, e.g. by providing an end fitting having multiple ports, eluate from different regions of the column can be processed differently. The present invention may therefore, for example, be practiced using a conventional HPLC system wherein one portion of the eluate flow is reacted and directed to a detector and another portion is sent processed in another way without being reacted. Even when the eluate is reacted and processed as ne portion only, the invention is applicable to conventional columns by virtue of requiring only a modified end fitting (flow distributor) and preferably split frit.

The present invention may also be practiced in which only one eluate flow leaves the column and is reacted. Such an embodiment represents a simple implementation of the invention, i.e. with a single eluate flow being reacted. In other words, there is no need in some embodiments to have a split flow of eluate, with different portions of eluate flow being either reacted or not reacted or reacted differently. This may be achieved for example using apparatus described above with reference to the Figures and blocking or capping, for example, the central port so that only a single portion of eluate in the peripheral region is reacted by supplying reactant via at least one peripheral port and extracting reacted eluate product via at least one other peripheral port. If such reactions on single portions only are required, then such means as described above for segmenting the eluate at the outlet (e.g. a split frit) may not be necessary. Moreover, in such embodiments, the flow distributor may be configured with only a required number (one or more) of reactant ports to enable reactant flow into the outlet and a required number (one or more) of product ports to receive and transmit product but without any other ports than these.

Using apparatus as described above with reference to the Figures, various implementations of the present invention may be achieved.

Figure 10:
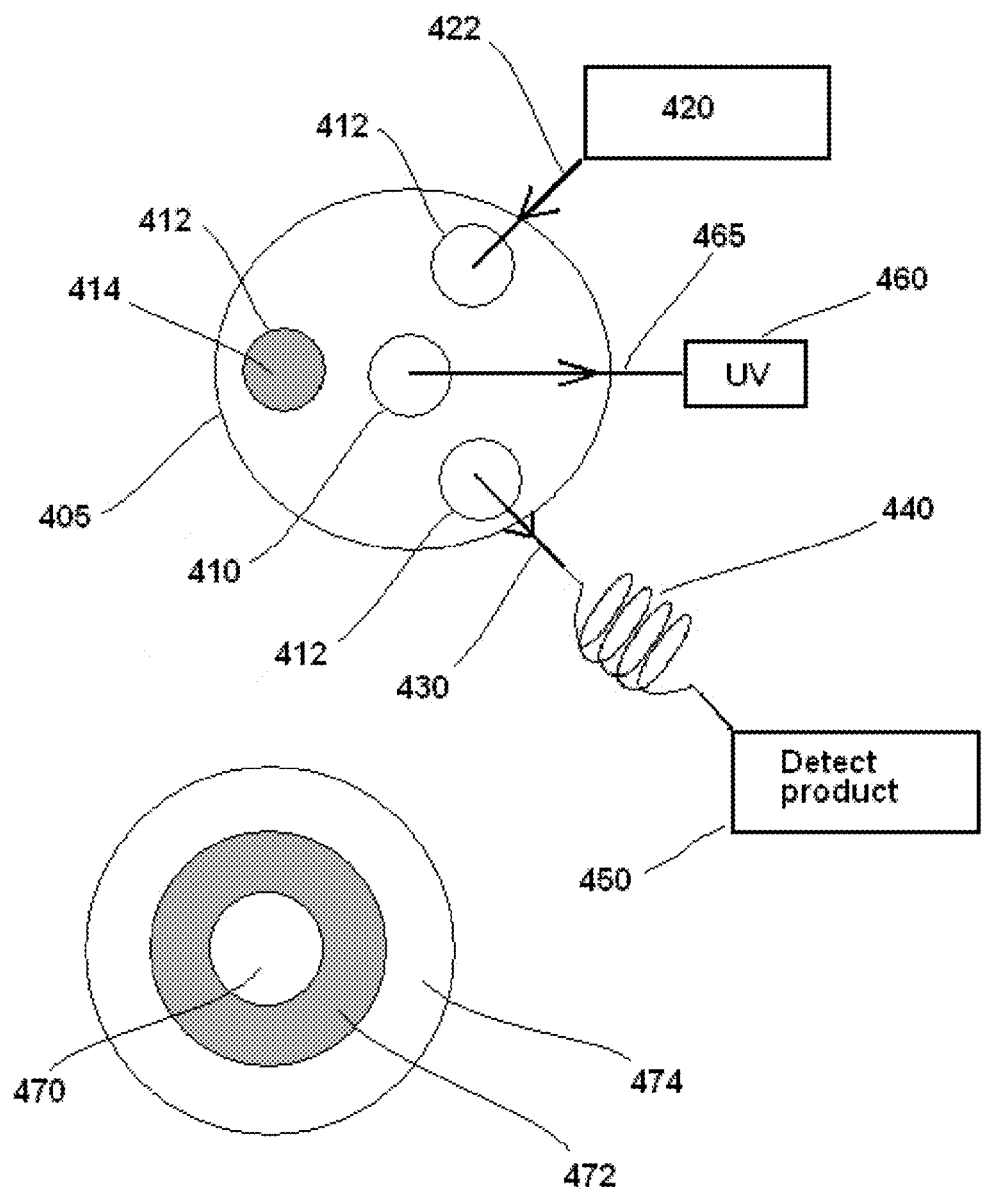
FIG. 10 shows schematically an embodiment for performing reaction chromatography according to the present invention.

A reaction chromatography embodiment is shown schematically in FIG. 10. A column fitted at its outlet end with a flow distributor 405, which may be one of the embodiments shown in FIGS. 6, 7 and 9, is shown end-on. The flow distributor is preferably in the form of an end fitting that is fitted to the end of the chromatography column as previously described. Thus, the embodiment uses a segmented parallel flow column, such as described herein, for reaction chromatography. A single central port fluid port 410 and three peripheral fluid ports 412 are shown. A first one of the peripheral fluid ports 412 is closed with a cap 414. A second one of the peripheral ports 412 is connected to a reactant source 420 which comprises a reservoir of reactant and a pump to supply a stream of reactant 422 into the second peripheral port 412. The second peripheral port 412 is thus a reactant port. The reactant mixes with eluate eluting from the peripheral region of the column that has passed through the outer frit section and the mixture of reactant and eluate from the column exits the flow distributor via a third one of the peripheral ports 412 as a reacted eluate flow 430. The third peripheral port 412 is thus a product port. Reaction occurs between one or more components in the eluate and the reactant. The reaction may begin in the flow distributor and may continue downstream of the distributor. Thus, herein, the term reacted eluate does not necessarily mean fully reacted eluate but only that at least mixing of reactant and eluate has taken place and reaction has at least begun to occur or will occur downstream. An optional reaction coil 440 may be supplied for the reaction to proceed downstream of the flow distributor. This may be useful where the reaction is slow but may not be required where the reaction is sufficiently fast.

The reactant, for example, may be DPPH solution for reaction with antioxidant components in the eluate. This reaction results in decolorisation of the DPPH solution, which can be detected, e.g. at 500 nm by a UV detector. The reaction product is detected downstream at a detector 450, which, for example, could be the mentioned UV detector.

The reactions can be timed to occur when they are required, e.g. to correspond to the appearance at the outlet of a target component. Since chromatographic migration of components through the column is predictable, the application of the reactant into the outlet at a particular time can be carried out. Thus, the reactant can be timed to flow into the outlet when it is required, e.g. to correspond to the appearance at the outlet of a target component. This procedure is performed whenever a target component elutes.

It will be appreciated that in other embodiments, the peripheral fluid port 412 closed with cap 414 could instead not be fitted with a cap but be connected with the outflow from the other peripheral fluid port that transmits the reacted product to the detector.

In addition to the reactant port and product port, eluate flows from the column and flow distributor via the central port 410. This central port is aligned with the central frit section and receives eluate flow from the centre of the column bed. Since this central port and the central portion of eluate flow that it communicates with are not in fluid communication with any of the other ports or the peripheral portion of eluate that is reacted, the central eluate flow 465 through the central port remains unreacted. This central, unreacted eluate 465 is detected as usual at a detector 460, which may be a typical HPLC type detector such as UV detector.

A split frit, in particular an annular frit arrangement, is used with the reaction chromatography apparatus of FIG. 10 so that it enables the eluate flow to be split into the two portions (central and peripheral) and enables differences between the unreacted, native eluate and the reacted eluate to be observed and so changes in the system to be gauged. A suitable annular frit arrangement is shown schematically in FIG. 10 that comprises a central frit section 470, an annular non-porous flow barrier 472 and an annular outer frit section 474. The central frit section 470 and thus the central portion of eluate flowing therethrough is in fluid communication with the central fluid port 410 but is fluidly separated by the flow barrier 472 from the peripheral eluate flow. The annular frit section 474 and thus the peripheral portion of eluate flowing therethrough is in fluid communication with the outer peripheral fluid ports 412. With the eluate portions divided and fluidly separated in this way, one portion (peripheral in this case) can be reacted as described above whilst the other portion (central in this case) passes unreacted to a processing unit (detector).

Figure 11:
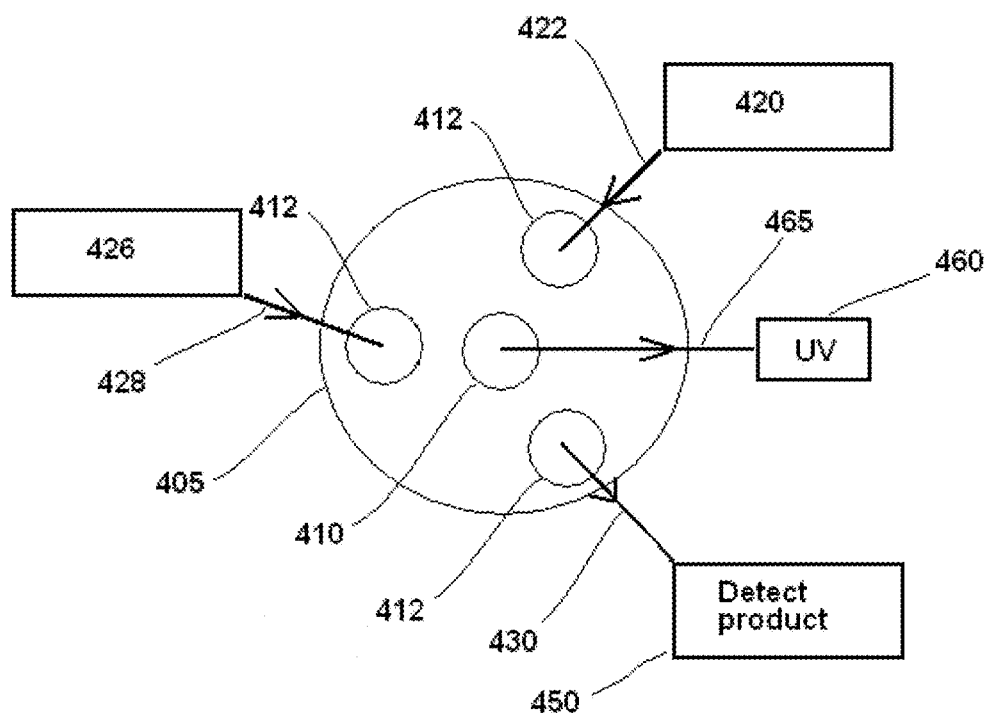
FIG. 11 shows schematically a further embodiment for performing reaction chromatography according to the present invention.

A similar reaction chromatography embodiment to that of FIG. 10 is shown schematically in FIG. 11. The arrangement is mostly the same but in this case the first peripheral port 412 is also a reactant port so that there are two reactant ports in all. The first peripheral port (reactant port) in this case can flow a second reactant stream 428 into the outlet from a second reactant source 426. The peripheral eluate portion in this case mixes with both the first and second reactants and the combination exits as product stream 430 via the third peripheral port 412 as before. A reaction coil is not shown in this embodiment as this is merely optional for the invention.

Figure 12:
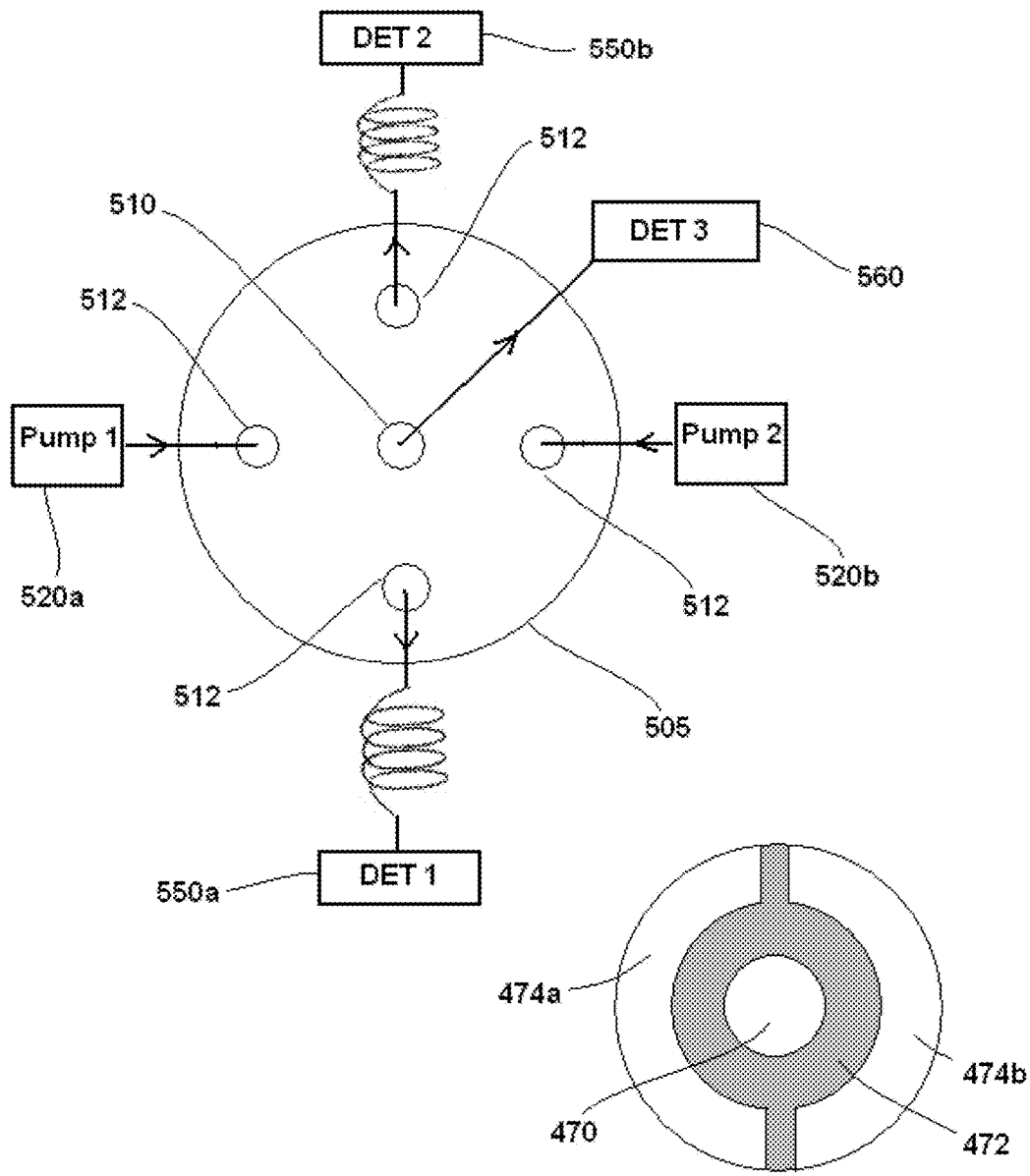
FIG. 12 shows schematically another embodiment for performing reaction chromatography according to the present invention.

FIG. 12 shows schematically an embodiment of the invention for performing two separate reactions simultaneously (multiplexed reactions). In the design shown, a total of five fluid ports are provided in the flow distributor 505, comprising four peripheral ports 512 and one central port 510. Once again an annular frit is provided but in this embodiment, the outer annular frit section 474 is split into two further sections 474a and 474b, such that each further section resembles an approximately semi-circular shape. The two outer frit sections 474a and 474b are fluidly separated from each other (and from the central frit section 470) by the flow barrier 472. This enables two separate reactions to be performed due to the absence of cross-flow in reagents through the frit. One reaction may be performed on the eluate flowing through one frit peripheral section 474a while another reaction may be performed on the eluate flowing through the other peripheral frit section 474b. Also, the two fluidly separated peripheral portions of eluate are separated from a central portion of eluate flowing through central frit section 470.

Each frit section 474a and 474b is in fluid communication with both a reactant port and a product port. The frit section 474a is in communication with a first peripheral port 512 which is a reactant port fed with a first reactant from a first pumped reactant source 520a. The frit section 474a is furthermore in communication with another peripheral port 512 which is a first product port for receiving the product of the mixed first reactant and eluate and sending the product stream (via optional reaction coil shown) to a first detector 550a. The other frit section 474b is in communication with a further peripheral port 512 which is a reactant port fed with a second reactant from a second pumped reactant source 520b. The other frit section 474b is furthermore in communication with yet another peripheral port 512 which is a second product port for receiving the product of the mixed second reactant and eluate and sending the product stream (via optional reaction coil shown) to a second detector 550b. The two different product streams may optionally exit through a loop. The product streams may be independently detected. As mere examples of different reactants, the first reactant could be DPPH reagent for antioxidants and the second reagent could be Xanthine oxidase used as part of a biodetector, e.g. in anti arthritic studies.

As in the previous embodiment, in addition to the peripheral reactant ports and product ports, eluate flows from the column and flow distributor via the central port 510. This central port is aligned with the central frit section 474 and receives eluate flow from the centre of the column bed. Since this central port and the central portion of eluate flow that it communicates with are not in fluid communication with any of the other ports or the peripheral portion of eluate that is reacted, the central eluate flow through the central port 510 remains unreacted. This central, unreacted eluate is independently detected as usual at a detector 560, which may be a typical UV detector.

The invention may have application in the following situations, for example: synthesizing compounds on a small scale e.g. nano-scale; natural product screening; protein digestions, optionally where digests could flow directly to a mass spectrometer or to a $2^{nd}$ dimension chromatography column; catalytic processes, e.g. in the food or pharmaceutical industries.

EXAMPLES

Details of experiments and results are given below to further illustrate the invention by way of examples.

Inventive Example

Reaction chromatography according to the present invention was performed using a segmented parallel flow column with end fitting as shown in FIG. 6. Modifications were made at the fluid ports of the end fitting as shown schematically in FIG. 13. The mobile phase was flowed through the column 600 from its inlet to outlet by means of upstream pump 1 (not shown). At the end of the column was fitted a four port, parallel segmented flow end fitting 600, as described above (and as shown in FIG. 6). An annular segmented frit and flow directing cap, as described hereinabove, were utilised to segment the eluate flow at the outlet. Two of the ports 610 were sealed with plugs (not shown), being the central port and one of the peripheral ports. One of the peripheral ports 612 constituted a reactant port and delivered a flow of reactant into the column outlet from a reactant source 614 that was supplied by a pump 2. The final one of the peripheral ports 622 constituted a product port and carried a flow of reacted eluate product away from the column outlet to a UV detector 624 and from there to a waste reservoir 630. The location of a reaction coil (when used) is shown by reference 640. The eluate exiting the column in this way can undergo efficient reaction with the reactant introduced into the peripheral zone of the end fitting.

Comparative Example

Figure 13:
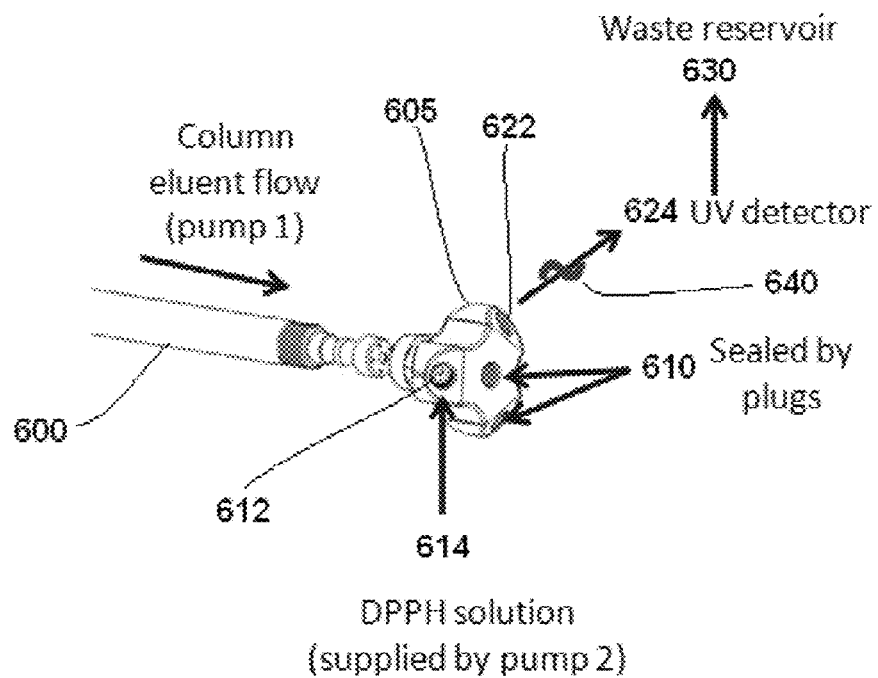
FIG. 13 shows yet another embodiment of the invention for performing reaction chromatography, being a modification of the embodiment shown in FIG. 6.
Figure 14:
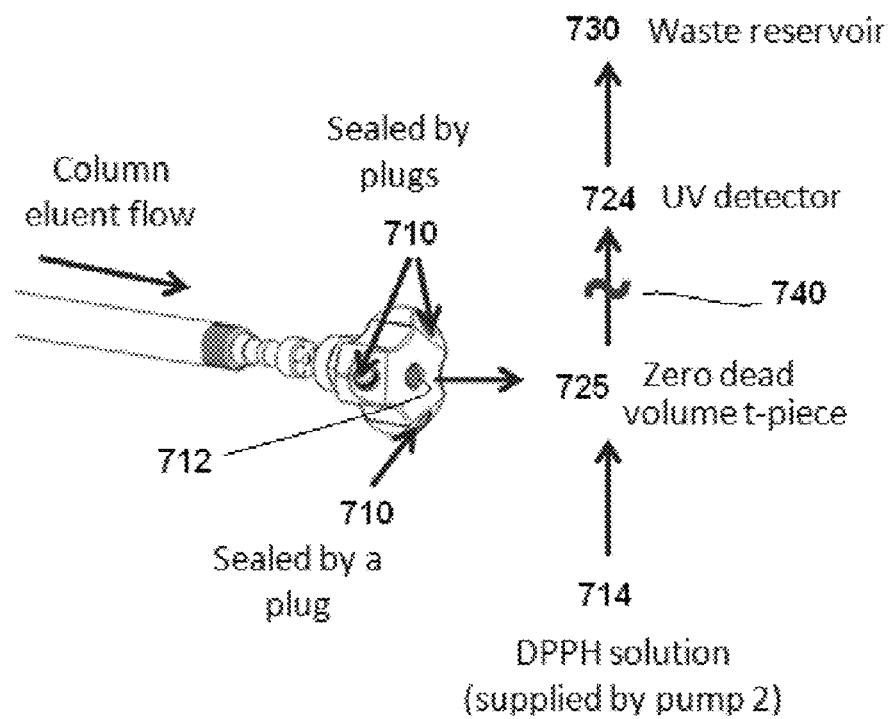
FIG. 14 shows an embodiment similar to that shown in FIG. 13 but altered to simulate a prior art method of performing reaction chromatography.

For comparison to the example embodying the present invention shown in FIG. 13, a conventional reaction chromatography configuration was constructed in which the same column and four port end fitting as shown in FIG. 13 was used but with the alterations shown in FIG. 14. In the comparative case, all three peripheral ports 710 were plugged and only the central port 712 was open to direct the eluate into a zero dead volume t-piece 725 located separate from and downstream of the column. In this case, reactant was delivered into the t-piece 725 from a reactant source 714 that was supplied by a pump 2. The product was carried away from the t-piece 725 to a UV detector 724 and from there to a waste reservoir 730. The location of a reaction coil (when used) is shown by reference 740.

To test the two set-ups, reaction chromatography was performed for the analysis of coffee with simultaneous DPPH and UV detection. Espresso coffee was analysed using HPLC with DPPH (1,1-Diphenyl-2-picryl-hydrazyl) and UV detection.

Espresso coffee was used as the sample, as it is known to contain numerous antioxidants. Reaction between the DPPH radical and an antioxidant results in decolorisation of the DPPH solution. This decolorisation can be detected at ~500 nm using a UV detector. The DPPH reaction is relatively slow, therefore most conventional DPPH detection processes employ reaction coils (commonly 800 uL in volume), resulting in substantial band broadening and leading to poor peak shape and resolution.

The tests illustrated that post column reagents can be mixed with eluting sample within the end fitting of the HPLC column (Inventive Example) and a reaction that can be monitored. The resulting chromatograms were compared with the chromatograms obtained using the Comparative Example set-up of FIG. 14 and the results are described below.

Experimental Details

Sample Preparation:

30 mL of "Ristretto" espresso coffee was freshly prepared using a Delonghi espresso machine. The coffee was filtered using a 0.45 um PVDF syringe filter and allowed to cool to room temperature prior to analysis.

Preparation of DPPH Reagent:

A solution of 0.05 mgmL$^{-1}$ DPPH in methanol was accurately prepared using volumetric glassware.

Chromatographic Column:

All experiments were conducted using a HYPERSIL GOLD®, Gold reversed phase column (100×4.6 mm) fitted with a four-way parallel segmented flow end fitting as shown in FIGS. 13 and 14.

Chromatographic Conditions:

Ristretto coffee (20 mL injection volume) was analysed using a SHIMADZU® analytical HPLC system which comprised a SHIMADZU® LC-20ADvp quaternary pump, SHIMADZU® SIL-10ADvp auto injector, SHIMADZU® SPD-M10Avp PDA detector and a Degassex model DG-440 inline degasser unit.

Separation was achieved using a water/methanol: gradient starting from 5% (methanol) and finishing at 100% methanol. The gradient rate was 2%/min. The mobile phase flow rate was 1.0 mLmin$^{-1}$.

Chromatograms were extracted at 275 nm for UV detection and 500 nm for the DPPH reaction using simultaneous dual wavelength detection.

DPPH was added to the flow stream using a SHIMADZU® LC-19ADvp quarternary pump at flow rates as described below.

Results

Experiments for both the Inventive Example and Comparative Example were conducted using 99 uL, 200 uL reaction coils and no coil (that is, eluent and reagent enter the detector through minimum tubing after mixing) using a DPPH:eluent flow rate ratio of 1.5:1. DPPH chromatograms and UV chromatograms are shown in the Figures now described for the Inventive Example and Comparative Example.

Results—No Reaction Coil

Figure 15A:
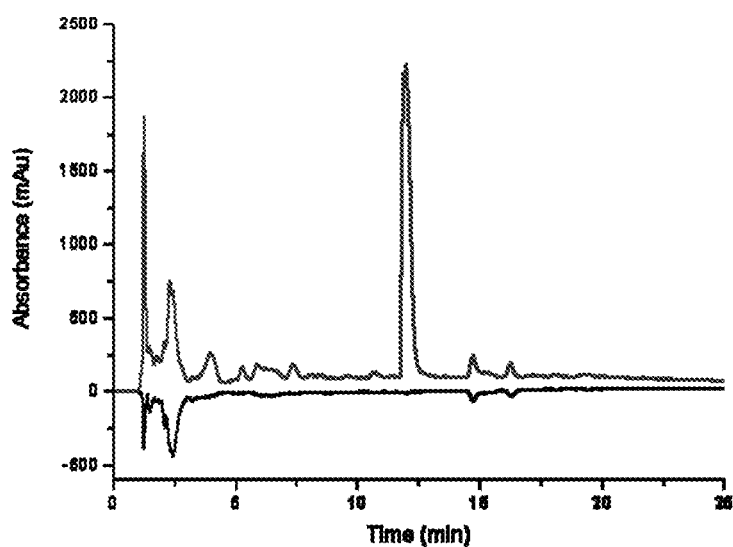
FIGS. 15A-D show the chromatogram for a Comparative Example with no reaction coil present.
Figure 15B:
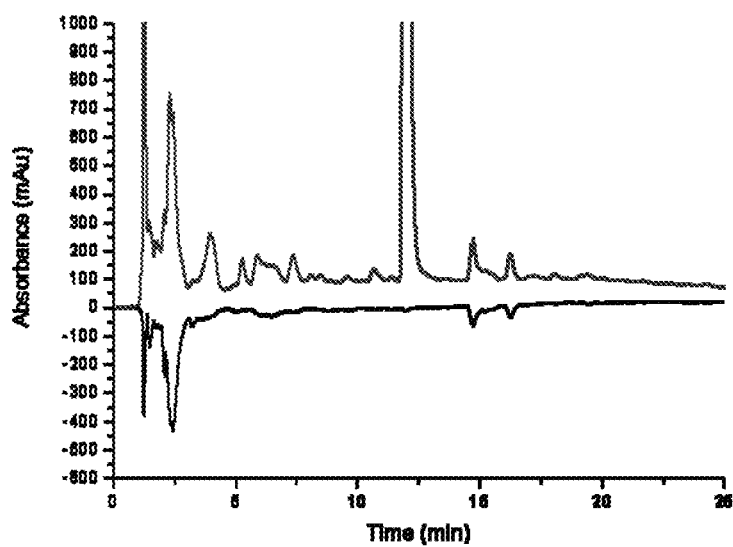
Figure 15C:
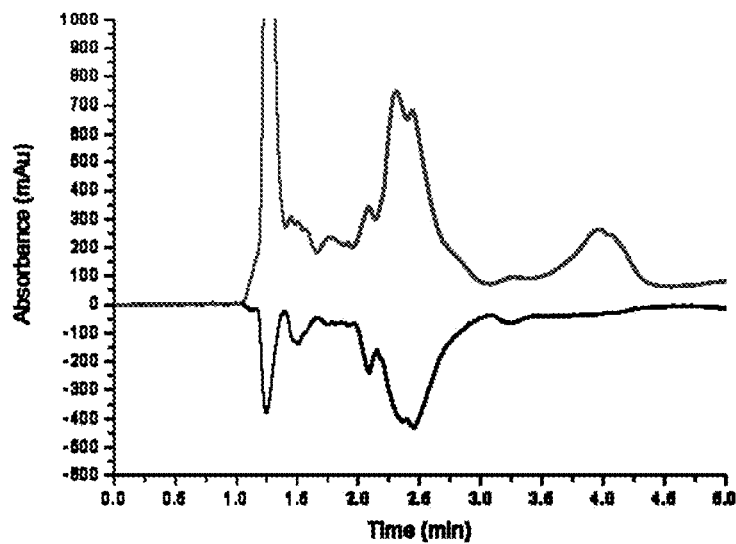
Figure 15D:
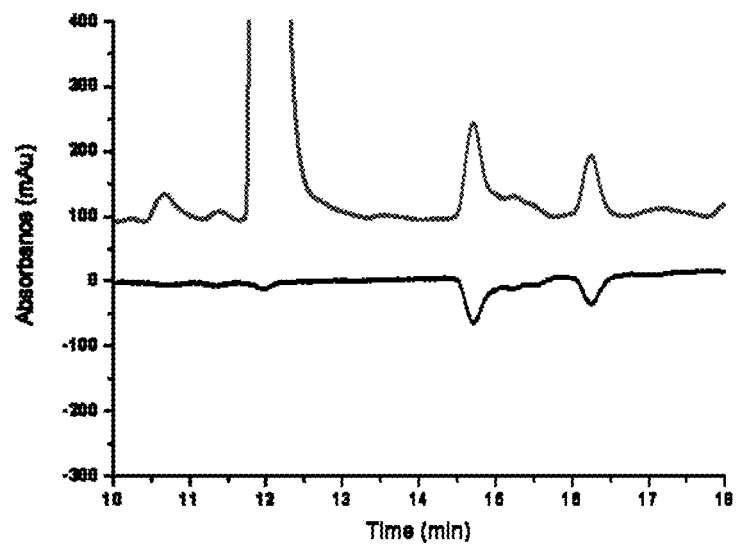

FIGS. 15A-D show the chromatogram for the Comparative Example with no reaction coil present (in each figure the upper trace is the UV chromatogram and the lower trace is the DPPH chromatogram). FIG. 15A shows the full chromatogram; FIG. 15B shows the zoomed in (intensity) full chromatogram; FIG. 15C shows the zoomed in 0-5 min region; and FIG. 15D shows the zoomed in 10 to 18 min region.

Figure 16A:
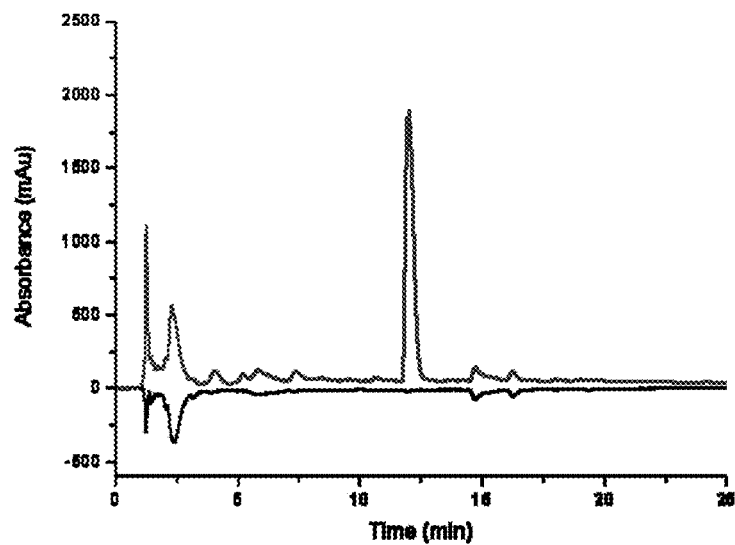
FIGS. 16A-D show the chromatogram for an Inventive Example with no reaction coil present.
Figure 16B:
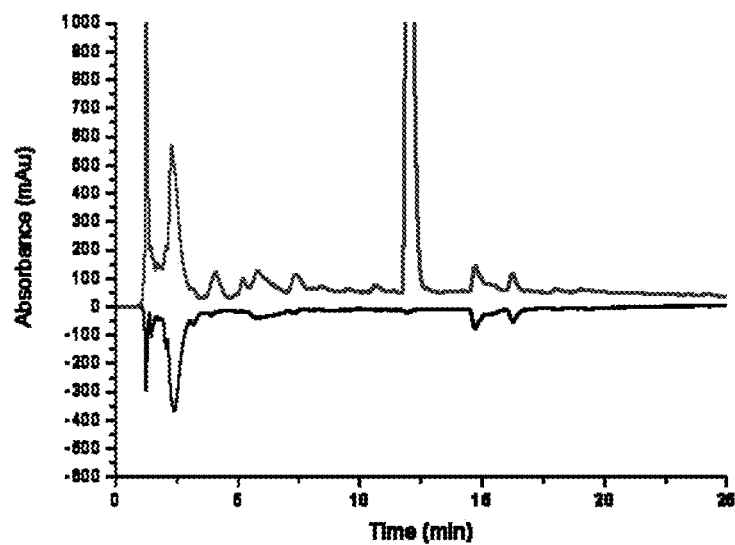
Figure 16C:
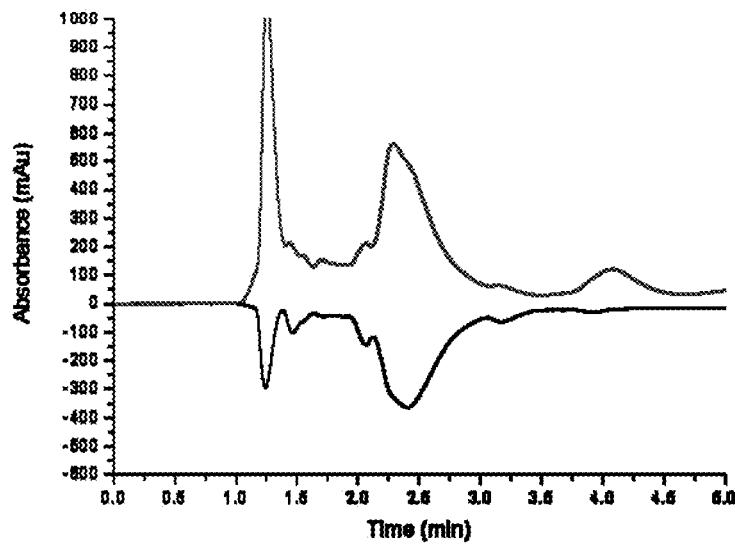
Figure 16D:
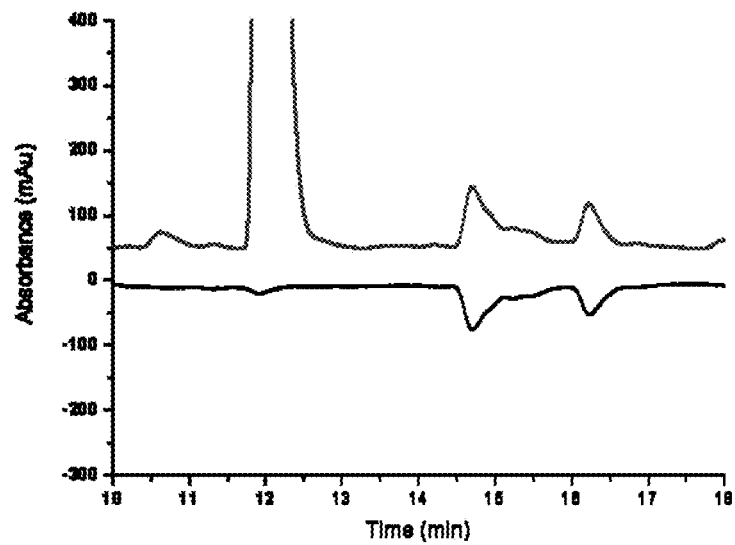

FIGS. 16A-D show the chromatogram for the Inventive Example with no reaction coil present (in each figure the upper trace is the UV chromatogram and the lower trace is the DPPH chromatogram). FIG. 16A shows the full chromatogram; FIG. 16B shows the zoomed in (intensity) full chromatogram; FIG. 16C shows the zoomed in 0-5 min region; and FIG. 16D shows the zoomed in 10 to 18 min region.

Results—99 μL Reaction Coil

Figure 17A:
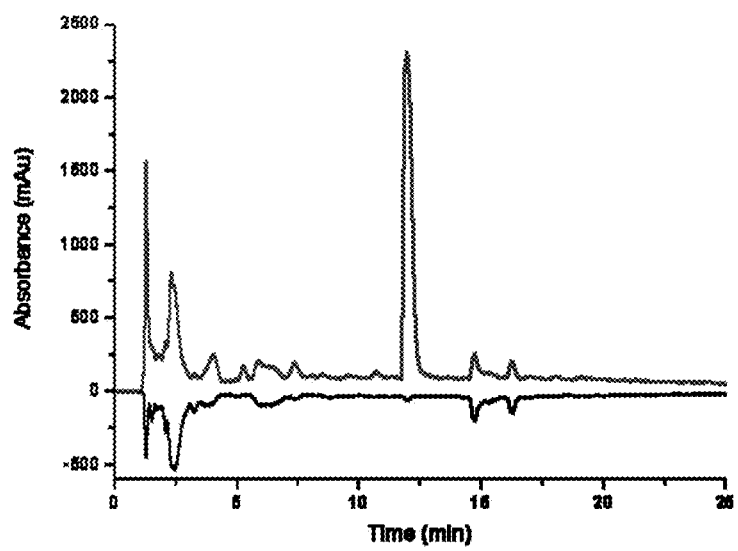
FIGS. 17A-D show the chromatogram for a Comparative Example with a 99 µL reaction coil present.
Figure 17B:
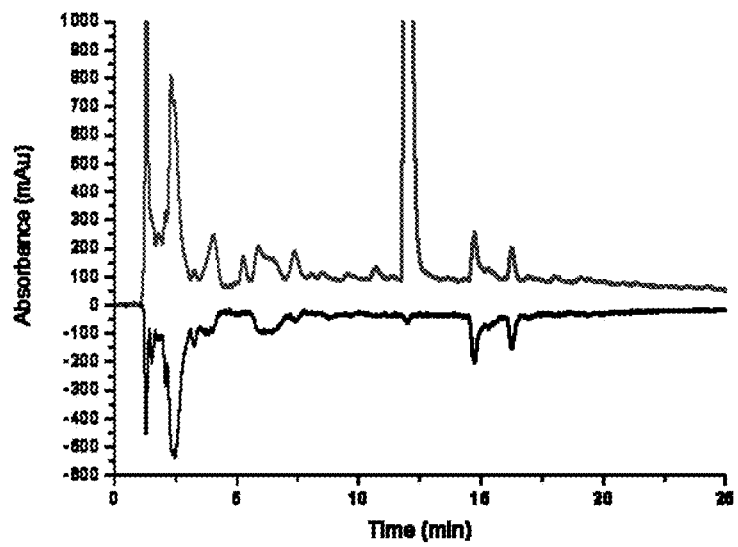
Figure 17C:
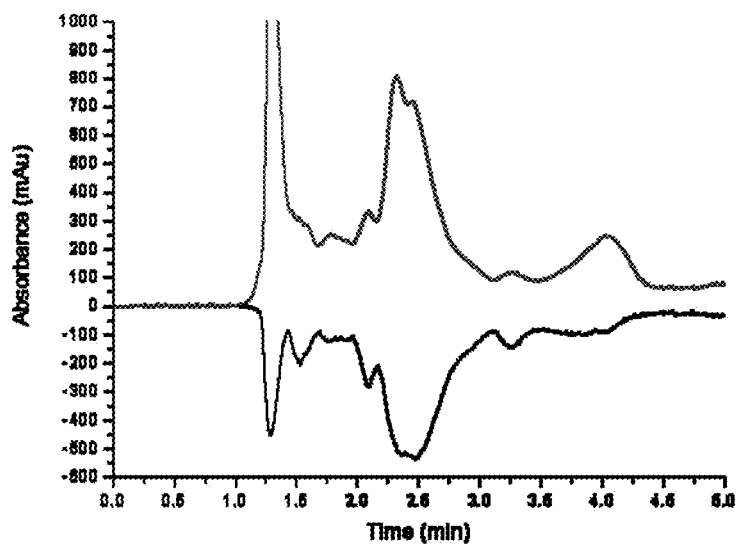
Figure 17D:
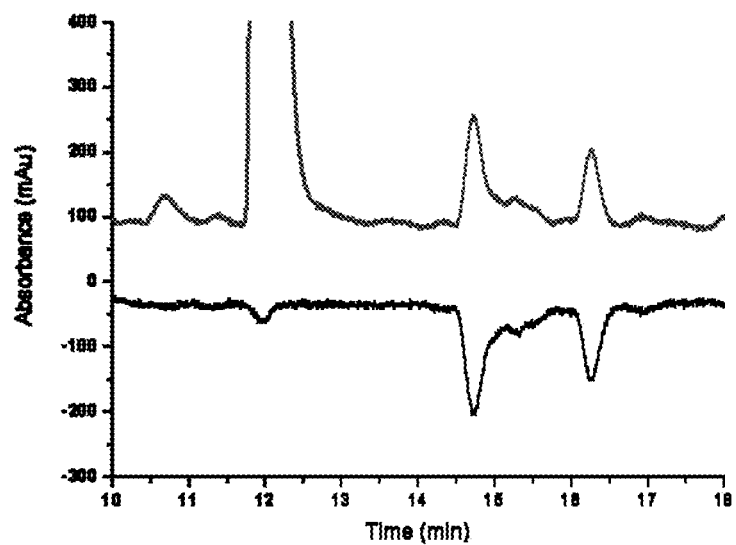

FIGS. 17A-D show the chromatogram for the Comparative Example with a 99 μL reaction coil present (in each figure the upper trace is the UV chromatogram and the lower trace is the DPPH chromatogram). FIG. 17A shows the full chromatogram; FIG. 17B shows the zoomed in (intensity) full chromatogram; FIG. 17C shows the zoomed in 0-5 min region; and FIG. 17D shows the zoomed in 10 to 18 min region.

Figure 18A:
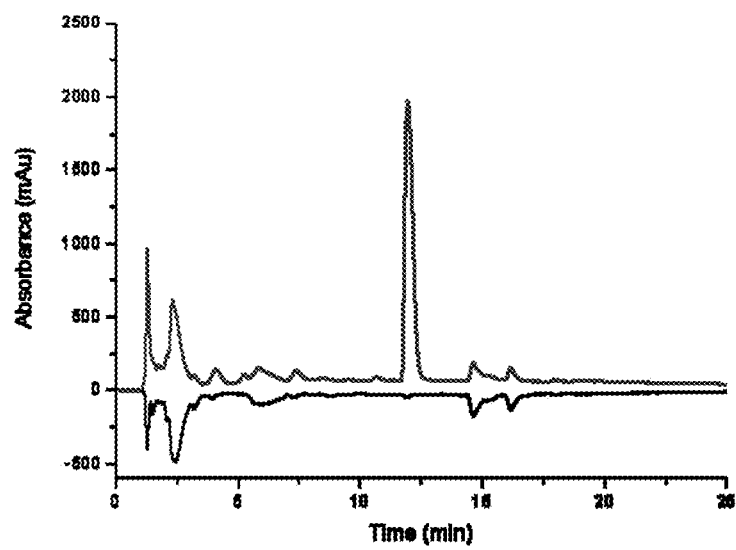
FIGS. 18A-D show the chromatogram for an Inventive Example with a 99 µL reaction coil present.
Figure 18B:
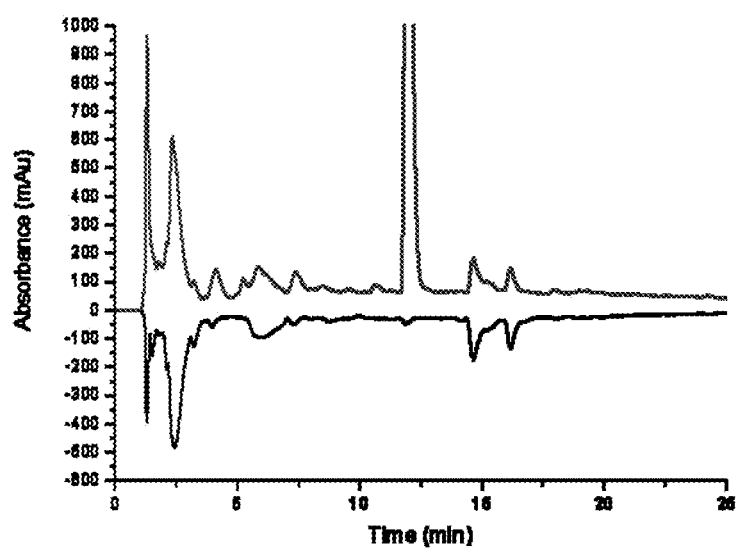
Figure 18C:
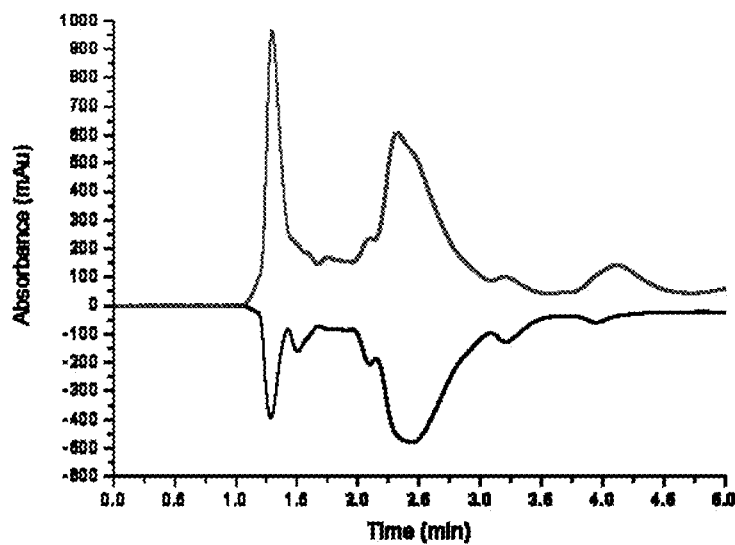
Figure 18D:
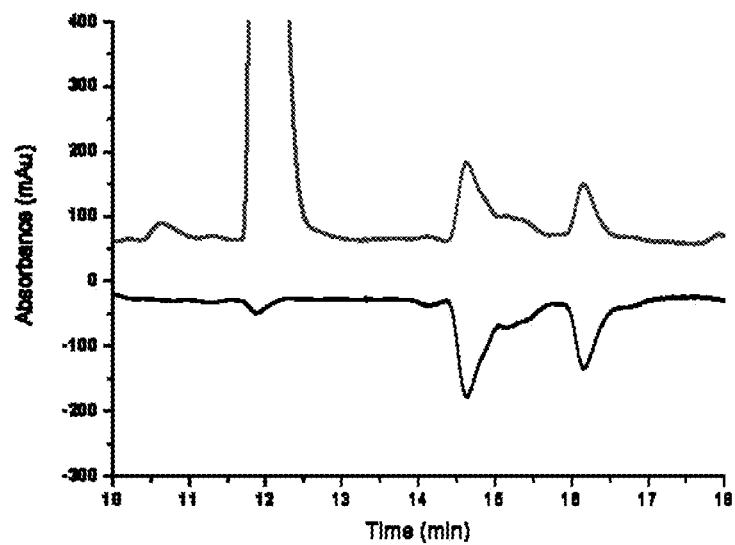

FIGS. 18A-D show the chromatogram for the Inventive Example with a 99 μL reaction coil present (in each figure the upper trace is the UV chromatogram and the lower trace is the DPPH chromatogram). FIG. 18A shows the full chromatogram; FIG. 18B shows the zoomed in (intensity) full chromatogram; FIG. 18C shows the zoomed in 0-5 min region; and FIG. 18D shows the zoomed in 10 to 18 min region.

Results—200 μL Reaction Coil

Figure 19A:
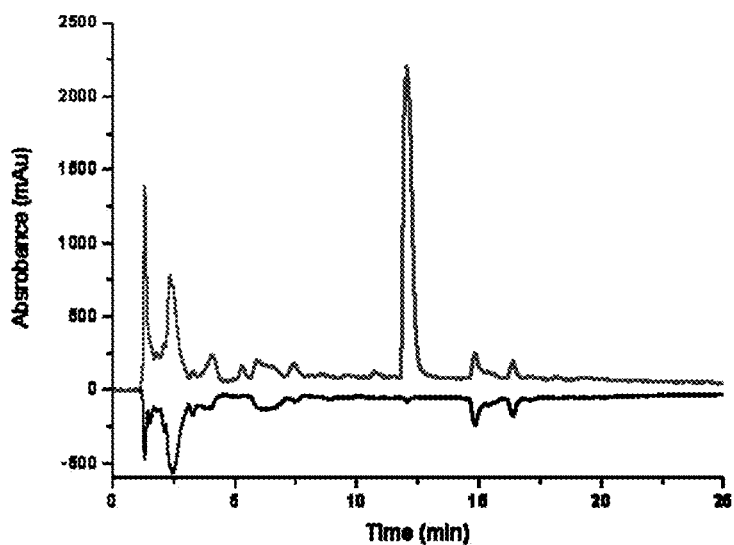
FIGS. 19A-D show the chromatogram for a Comparative Example with a 200 µL reaction coil present.
Figure 19B:
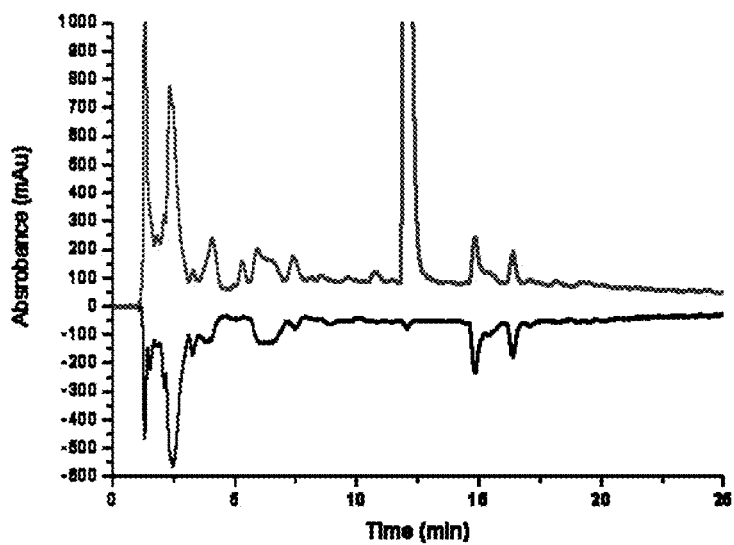
Figure 19C:
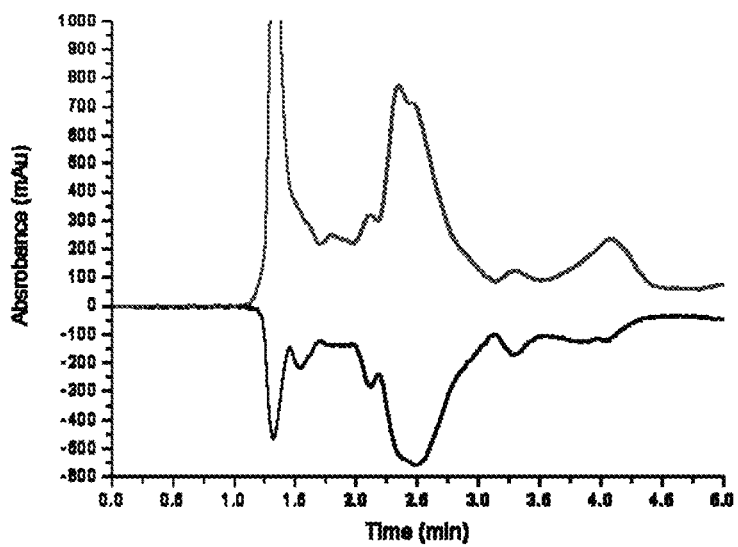
Figure 19D:
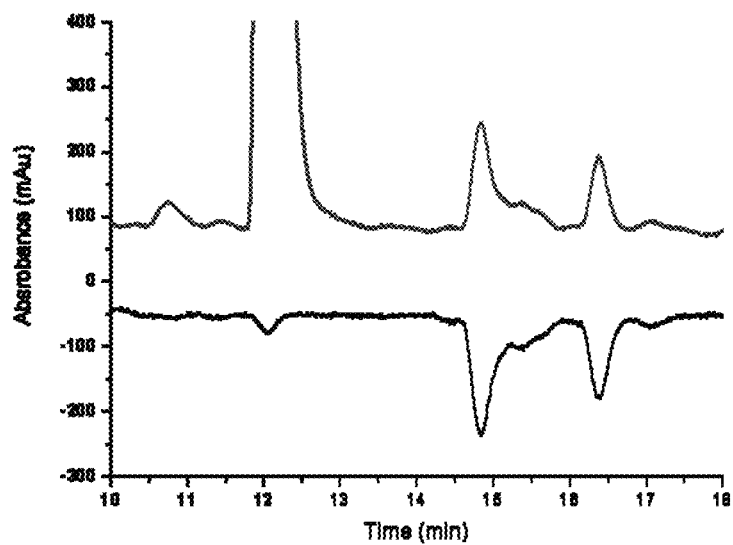

FIGS. 19A-D show the chromatogram for the Comparative Example with a 200 μL reaction coil present (in each figure the upper trace is the UV chromatogram and the lower trace is the DPPH chromatogram). FIG. 19A shows the full chromatogram; FIG. 19B shows the zoomed in (intensity) full chromatogram; FIG. 19C shows the zoomed in 0-5 min region; and FIG. 19D shows the zoomed in 10 to 18 min region.

Figure 20A:
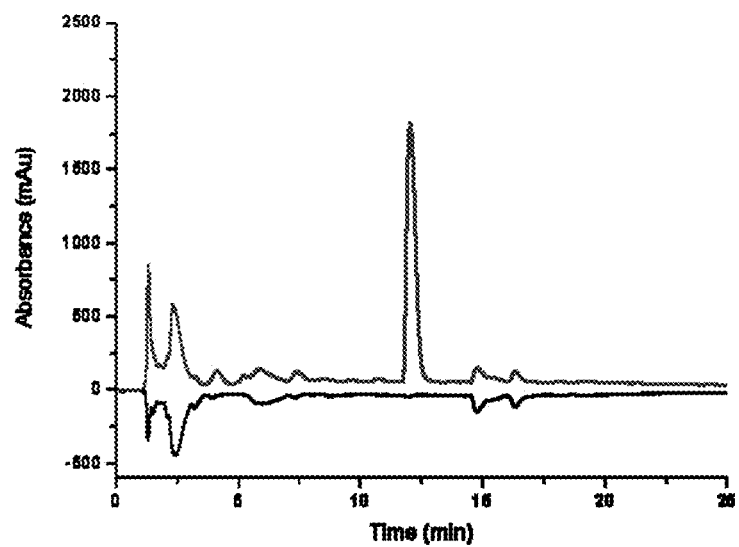
FIGS. 20A-D show the chromatogram for an Inventive Example with a 200 µL reaction coil present.
Figure 20B:
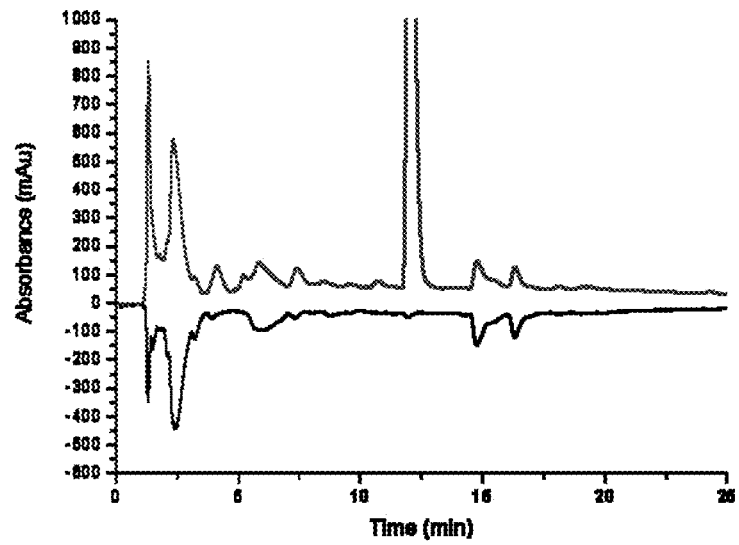
Figure 20C:
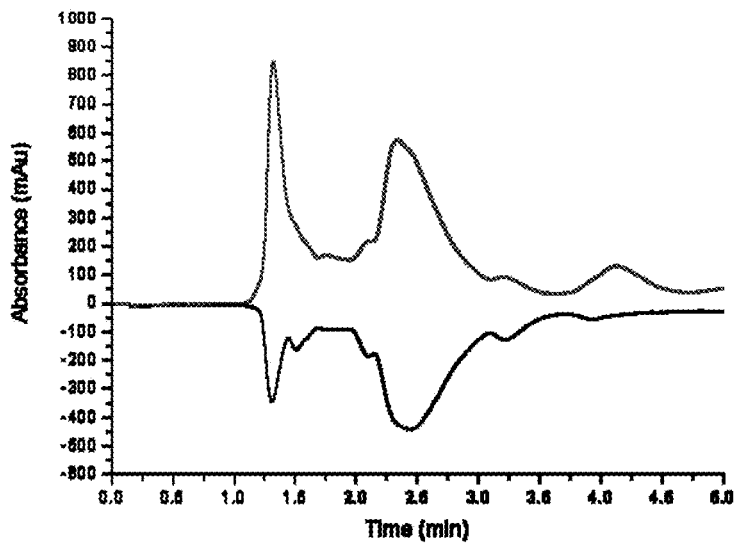
Figure 20D:
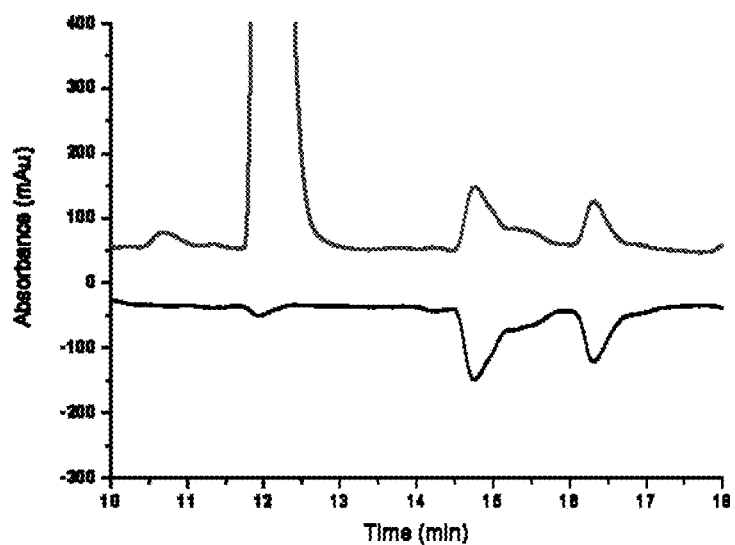

FIGS. 20A-D show the chromatogram for the Inventive Example with a 200 μL reaction coil present (in each figure the upper trace is the UV chromatogram and the lower trace is the DPPH chromatogram). FIG. 20A shows the full chromatogram; FIG. 20B shows the zoomed in (intensity) full chromatogram; FIG. 20C shows the zoomed in 0-5 min region; and FIG. 20D shows the zoomed in 10 to 18 min region.

Figure 21:
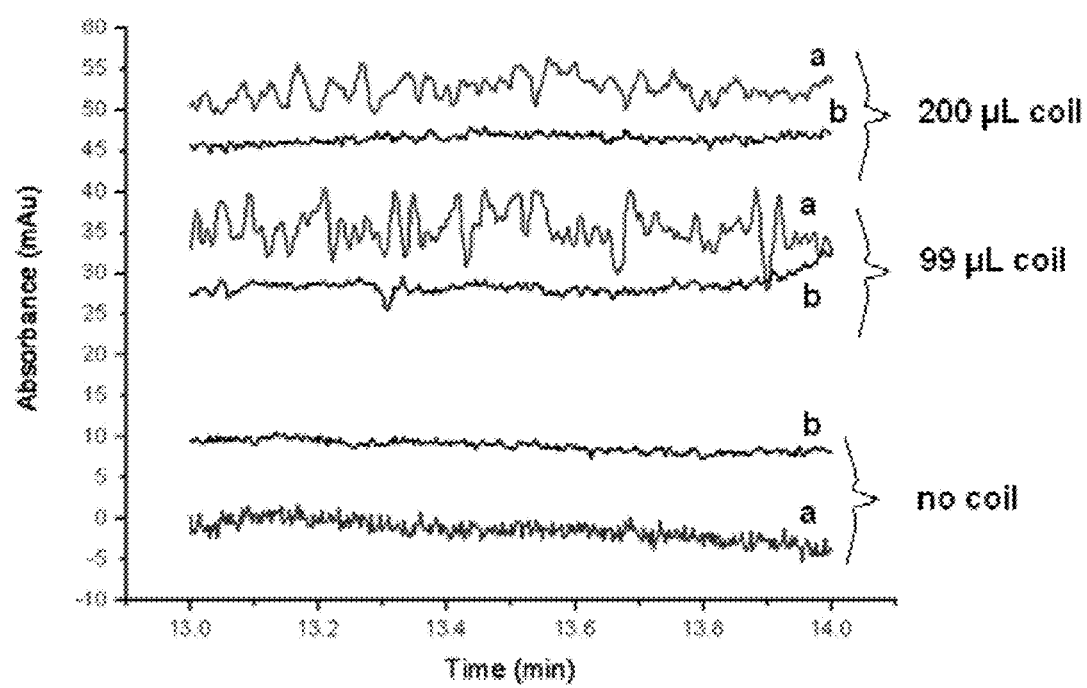
FIG. 21 shows a comparison of noise levels in chromatograms for both Comparative (a) and Inventive (b) Examples.

The Inventive Example enabled the DPPH to be readily decolourised. From the results it is evident that although the DPPH detection in the Comparative Example with post-column reaction is slightly more sensitive than the corresponding Inventive Example, the Inventive Example has significantly lower noise, giving an overall signal-to-noise advantage in that case. This is more clearly shown in FIG. 21 by comparing the results for both Comparative Examples (a) and Inventive Examples (b) and zooming in on the 13 to 14 min region. It is also evident from FIG. 21 that the noise in the Inventive Example remains approximately constant irrespective of reaction coil volume, which is not true for the Comparative Example. Thus, with the Inventive Example, it was possible to conduct simultaneous DPPH and UV analysis with substantially less noise and comparable sensitivity to the conventional post column reaction configuration of the Comparative Example.

Figure 22:
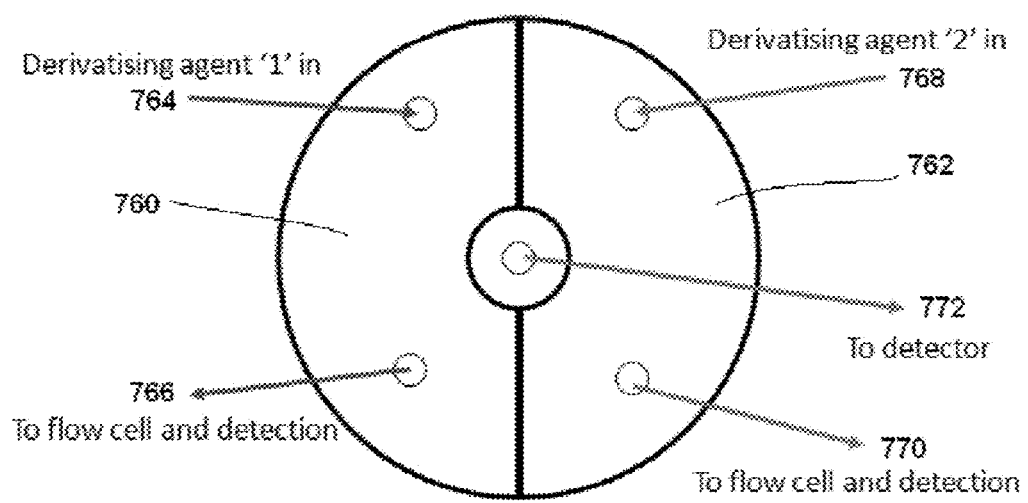
FIG. 22 shows schematically an embodiment for performing reaction chromatography according to the present invention utilizing a split flow frit with 5 exit ports.

One of the further benefits of the present invention is the ability to perform multiplex reactions and/or detection (i.e. simultaneous reactions and/or detection using multiple detectors). As shown schematically in FIG. 22 the end fitting could be modified, and preferably used with a segmented frit as described herein (see e.g. FIG. 12), so that one half of the fitting 760 reacts one portion of eluate at the outlet by flowing in a reactant, e.g. derivatising agent 1, through port 764. The combined eluate and derivatising agent product mixture then exits through port 766 to a flow cell and detection. At the same time, the other half of the fitting 762 reacts another portion of eluate at the outlet by flowing in a different reactant, e.g. derivatising agent 2, through port 768. This second combined eluate and derivatising agent product mixture then exits through port 770 to a second flow cell and detection. A third portion of eluate flow 772 may also be detected separately, which preferably has not undergone a reaction and so can be used to gauge changes compared to the reacted flows.

A large range of possible uses of the present invention include: the selective digestion of proteins/peptides with enzymes, e.g. such as trypsin; the screening of biologically active molecules; selective protein isolation; the derivatisation of compounds to facilitate detection, e.g. fluorescence detection; on-column stereoselective synthesis of compounds; chemiluminescence; and nanoscale synthesis.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A reaction chromatography apparatus, comprising:
   a chromatography column having a column outlet assembly;
   the column outlet assembly having a plurality of fluid ports;
   at least one reactant source in fluid communication with at least one of the plurality of fluid ports, wherein the reactant source is connected to the column outlet assembly and wherein no separate reaction equipment resides downstream of the chromatography column;
   at least one processing unit in fluid communication with at least one of the plurality of fluid ports.

2. An apparatus as claimed in claim 1 wherein the at least one processing unit is selected from the group consisting of: a detector, a fraction collector and another chromatography column.

3. An apparatus as claimed in claim 1, wherein there are two fluid ports.

4. An apparatus as claimed in claim 1 wherein at least one of the plurality of fluid ports is positioned to introduce a reactant flow only to a portion of an eluate flowing from a restricted radial region selected from a peripheral radial region of the chromatography column and a central radial region of the chromatography column, and, wherein at least one of the plurality of fluid ports is positioned to receive an at least partially reacted eluate flow.

5. An apparatus as claimed in claim 4 wherein the restricted radial region of the chromatography column is a peripheral radial region of the chromatography column.

6. An apparatus as claimed in claim 5 wherein at least one of the plurality of fluid ports receives a second portion of eluate flowing from a central radial region of the chromatography column.

7. An apparatus as claimed in claim 6 wherein the at least one of the plurality of fluid ports is in communication with a first processing unit comprising a first detector and wherein at least one of the plurality of fluid ports is in communication with a second processing unit comprising a second detector.

8. An apparatus as claimed in claim 1 wherein at least two of the plurality of fluid ports are positioned peripherally around a central axis of the chromatography column.

9. An apparatus as claimed in claim 8 having at least one of the plurality of fluid ports positioned on the central axis of the chromatography column.

10. An apparatus as claimed in claim 1 wherein the column outlet assembly comprises—a split frit having a plurality of frit sections whereby an eluate flow is segmented into a plurality of portions by the split frit.

11. An apparatus as claimed in claim 10 wherein a first frit section communicates with both a first reactant fluid port and a first product fluid port; and a second frit section communicates with both a second reactant fluid port and a second product fluid port.

12. An apparatus as claimed in claim 11 wherein the first reactant fluid port is in communication with a first reactant source and the second reactant fluid port is in communication with a second reactant source that is different from the first reactant source.

* * * * *